(12) United States Patent
Miyasa et al.

(10) Patent No.: US 8,696,123 B2
(45) Date of Patent: Apr. 15, 2014

(54) APPARATUS, METHOD, AND PROGRAM FOR PROCESSING INFORMATION

(75) Inventors: Kazuhiro Miyasa, Yokohama (JP); Akihiro Katayama, Yokohama (JP)

(73) Assignee: Canon Kabushiki Kaisha, Toky (JP)

( * ) Notice: Subject to any disclaimer, the term of this patent is extended or adjusted under 35 U.S.C. 154(b) by 168 days.

(21) Appl. No.: 12/911,331

(22) Filed: Oct. 25, 2010

(65) Prior Publication Data
US 2011/0102742 A1    May 5, 2011

(30) Foreign Application Priority Data
Oct. 29, 2009  (WO) .................. PCT/JP2009/068619

(51) Int. Cl.
*A61B 3/14* (2006.01)
*A61B 3/10* (2006.01)
*A61B 3/00* (2006.01)

(52) U.S. Cl.
USPC ............................. 351/206; 351/205; 351/246

(58) Field of Classification Search
USPC ................................................ 351/200–246
See application file for complete search history.

(56) References Cited

U.S. PATENT DOCUMENTS

| 5,920,373 A | 7/1999 | Bille |
| 7,604,351 B2 | 10/2009 | Fukuma |
| 8,194,261 B2 * | 6/2012 | Ooshio ........................ 358/1.13 |
| 8,414,122 B2 * | 4/2013 | Uchida ......................... 351/206 |
| 2003/0038921 A1 | 2/2003 | Neal |
| 2008/0252852 A1 | 10/2008 | Barth |
| 2009/0285354 A1 * | 11/2009 | Hirose et al. .................... 378/19 |

FOREIGN PATENT DOCUMENTS

| EP | 910984 A1 | 4/1999 |
| JP | 2005-506107 A | 3/2005 |
| JP | 2007-501677 A | 2/2007 |
| JP | 2008-246158 A | 10/2008 |

\* cited by examiner

*Primary Examiner* — Mohammed Hasan
(74) *Attorney, Agent, or Firm* — Canon USA Inc IP Division

(57) ABSTRACT

An information processing apparatus includes a determination unit configured to determine an incident angle of a signal light beam made incident on an object to be imaged in accordance with a structure of the object to be imaged and an instruction unit configured to send an instruction to capture a tomographic image of the object to be imaged on the basis of the signal light beam made incident on the object to be imaged at the determined incident angle.

38 Claims, 14 Drawing Sheets

APPARATUS, METHOD, AND PROGRAM FOR PROCESSING INFORMATION

TECHNICAL FIELD

The present invention relates to a technology for supporting capturing of an image when a tomographic image used for ophthalmic care is captured.

BACKGROUND ART

Ophthalmic tomography imaging apparatuses, such as an optical coherence tomography (OCT), can generate a three-dimensional image from retina layers. Such an image is generated by emitting a signal light beam to the retina, generating an interference light beam from a light beam reflected or scattered by each of the layers or boundary surfaces of the retina and a reference light beam, and forming an image using the interference light beam. By using this technology, the interior of the retina layers can be observed and, therefore, a disease can be correctly diagnosed. Accordingly, ophthalmic tomography imaging apparatuses have received a significant amount of attention in recent years.

It is important to correctly identify the layer structure of the retina in order to obtain an objective index for measuring the stage of disease progression (e.g., glaucoma progression). Examples of the index indicating glaucoma progression include a C/D ratio, which is a distance ratio between the edge of a depressed part of the optic papilla (referred to as a "cup") and the edge of the optic papilla (referred to as a "disc"), the area, depth, and volume of the cup, and the thickness of the optic nerve fiber layer located between the inner limiting membrane and the external limiting membrane.

FIG. 14 is a schematic illustration of tomographic images of the optic papilla. As shown in FIG. 14, two-dimensional tomographic images (B-Scan images) $T_1$ to $T_n$ of the optic papilla are obtained by capturing the images of the retina in the depth direction of the retina. Each of the two-dimensional tomographic images includes a plurality of scan lines that scan the retina in the depth direction (hereinafter referred to as "A-scan lines"). A Z-axis represents the direction of the A-scan. By sequentially performing raster-scanning in a predetermined area of a plane on the retina (an x-y plane), the three-dimensional data including $T_1$ to $T_n$ can be obtained. Since the layers of the retina have different reflectivities, an inner limiting membrane 1401, a pigment layer of the retina 1402, and an optic papilla 1403, for example, can be identified by analyzing the image.

Citation List

Patent Literature

PTL 1: Japanese Patent Laid-Open No. 2008-246158

The shape of the optic papilla differs from person to person. In one case of a patient, as shown in FIG. 14, the optic papilla may be depressed at an angle with respect to the surface of the retina. In such a case, if, as in existing OCTs, a signal light beam is emitted in a direction perpendicular to the surface of the retina, the signal light beam is blocked by the entrance portion of the depressed part and, therefore, a sufficient amount of the light signal does not travel inside the depressed part. Even when the light signal travels inside the depressed part, a returning light beam of the reflected or scattered signal light beam attenuates and, therefore, an area where the intensity of the signal is significantly reduced (e.g., an area 1404) appears. In addition, even when the optic papilla is not at an angle, an area which the signal does not reach appears if the signal light beam is emitted at an angle different from the direction of the depressed part.

In addition, even when the signal light beam is perpendicularly emitted, the light beam is attenuated due to red blood cells if an image artifact caused by veins or bleeding appears. Thus, the intensity of a light beam reflected by a tissue under the blood vessels is significantly reduced.

If, as described above, the signal cannot be received, the layer structure cannot be identified. As a result, information required for diagnosis cannot be acquired.

PTL 1 describes a technology for capturing an image while changing the irradiation position through preliminary image capturing. However, since, in this technology, the image of an area in which the intensity of a signal light beam is low, as an area of a cataract, is not captured, the technology cannot be applied when the image of a target tissue is captured.

SUMMARY OF INVENTION

To solve the above-described problem, the present invention provides an information processing apparatus including a determination unit configured to determine an incident angle of a signal light beam made incident on an object to be imaged in accordance with a structure of the object to be imaged and an instruction unit configured to send an instruction to capture a tomographic image of the object to be imaged on the basis of the signal light beam made incident on the object to be imaged at the determined incident angle.

Further features of the present invention will become apparent from the following description of exemplary embodiments with reference to the attached drawings.

DESCRIPTION OF EMBODIMENTS

According to an embodiment of the present invention, a scheme for capturing a tomographic image by controlling an irradiation angle of a signal light beam relative to the layer or boundary surface of the retina in order to capture an image suitable for diagnosis of the retina or image measurement is described. As an application, an example in which a tomographic image of a depressed part of the optic papilla is captured is described.

First Embodiment

According to a first embodiment, a three-dimensional tomographic image of the optic papilla is captured first using an OCT imaging method. Thereafter, the depressed part of the optic papilla is analyzed using the captured tomographic image. The irradiation angle of the signal light beam is determined so that the intensity of a returning or scattered light beam of the signal light beam at each analysis point of the depressed part is equal to a predetermined value. Subsequently, an image is further captured on the basis of the determined irradiation angle. Thus, an image indicating the shape of the depressed part of the optic papilla can be acquired.

Figure 1:
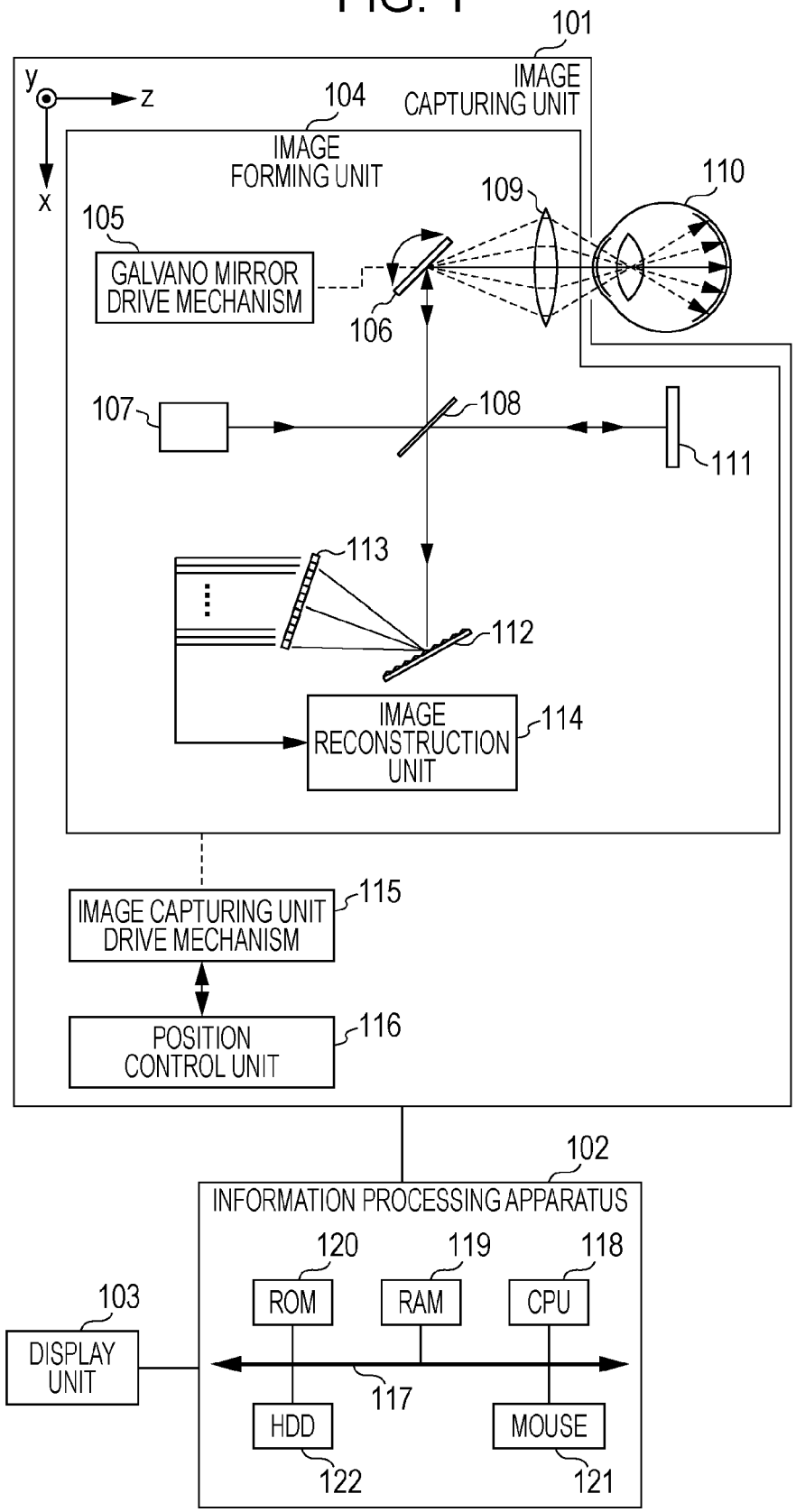
FIG. 1 illustrates the configuration of an OCT imaging system according to a first embodiment.
Figure 2A:
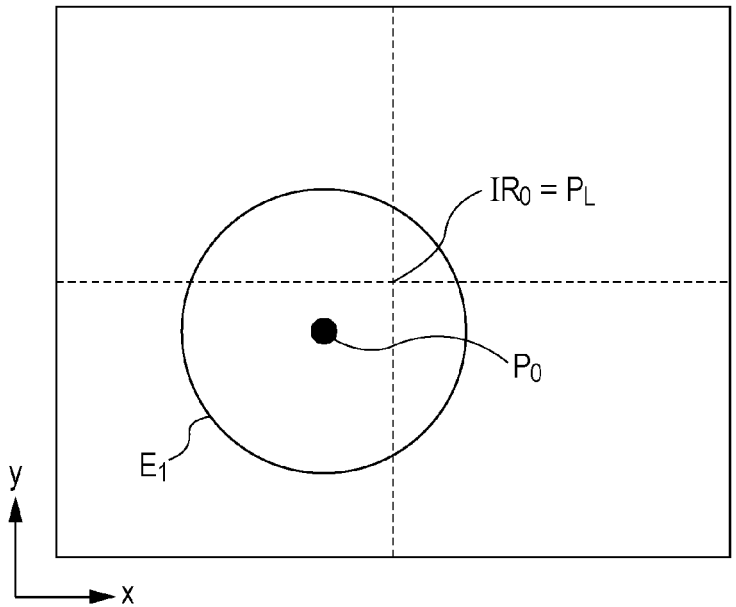
FIGS. 2A to 2C illustrate a positional relationship between the pupil and a signal light beam and a relationship between the pupil and the irradiation angle of the signal light beam.
Figure 2B:
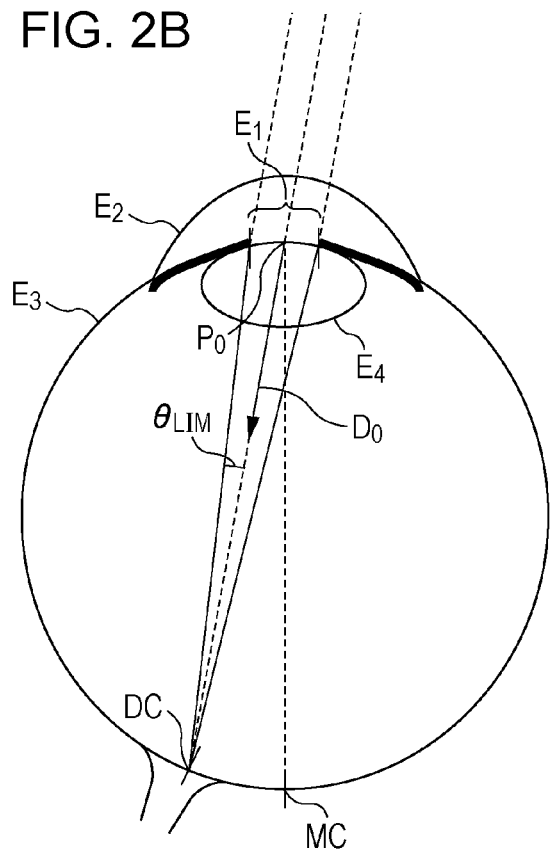
Figure 2C:
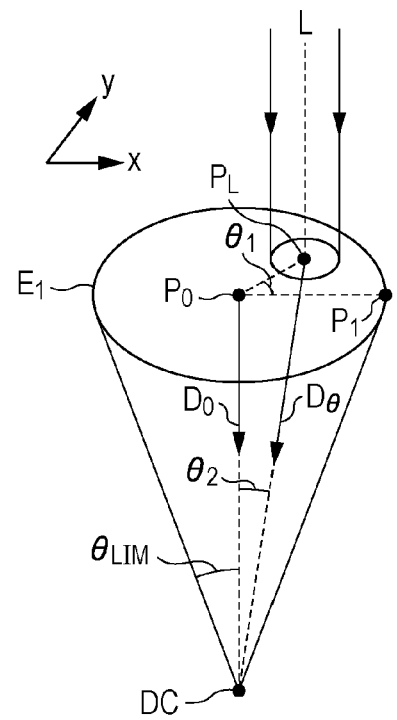
Figure 3:
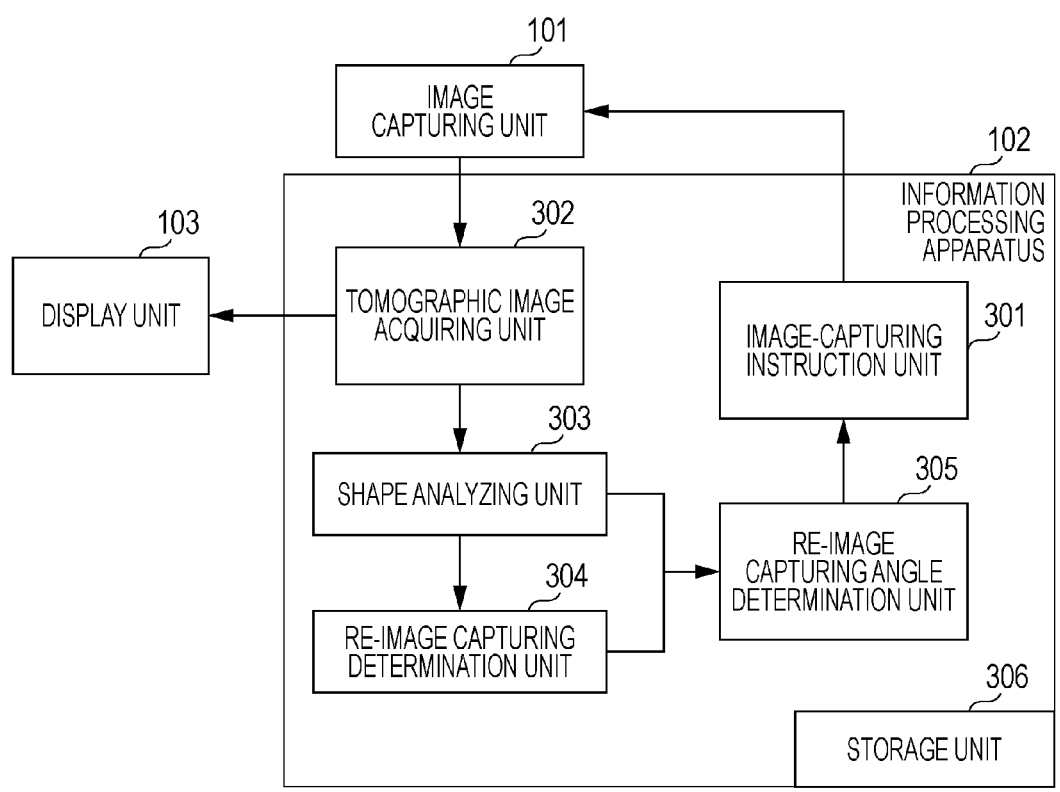
FIG. 3 is a functional block diagram of the OCT imaging system according to the first embodiment.
Figure 5:
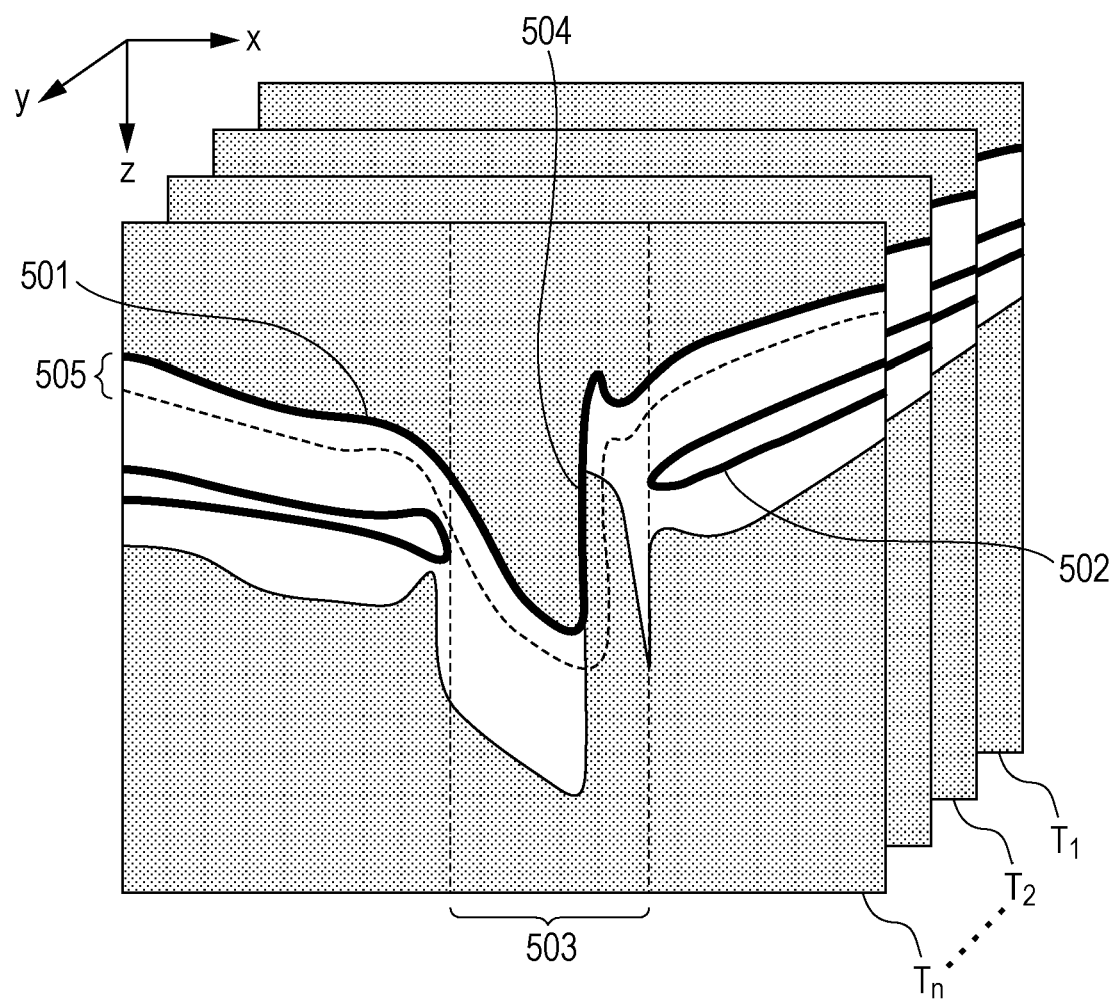
FIG. 5 illustrates extraction of the shape of the surface of the optic papilla.
Figure 6:
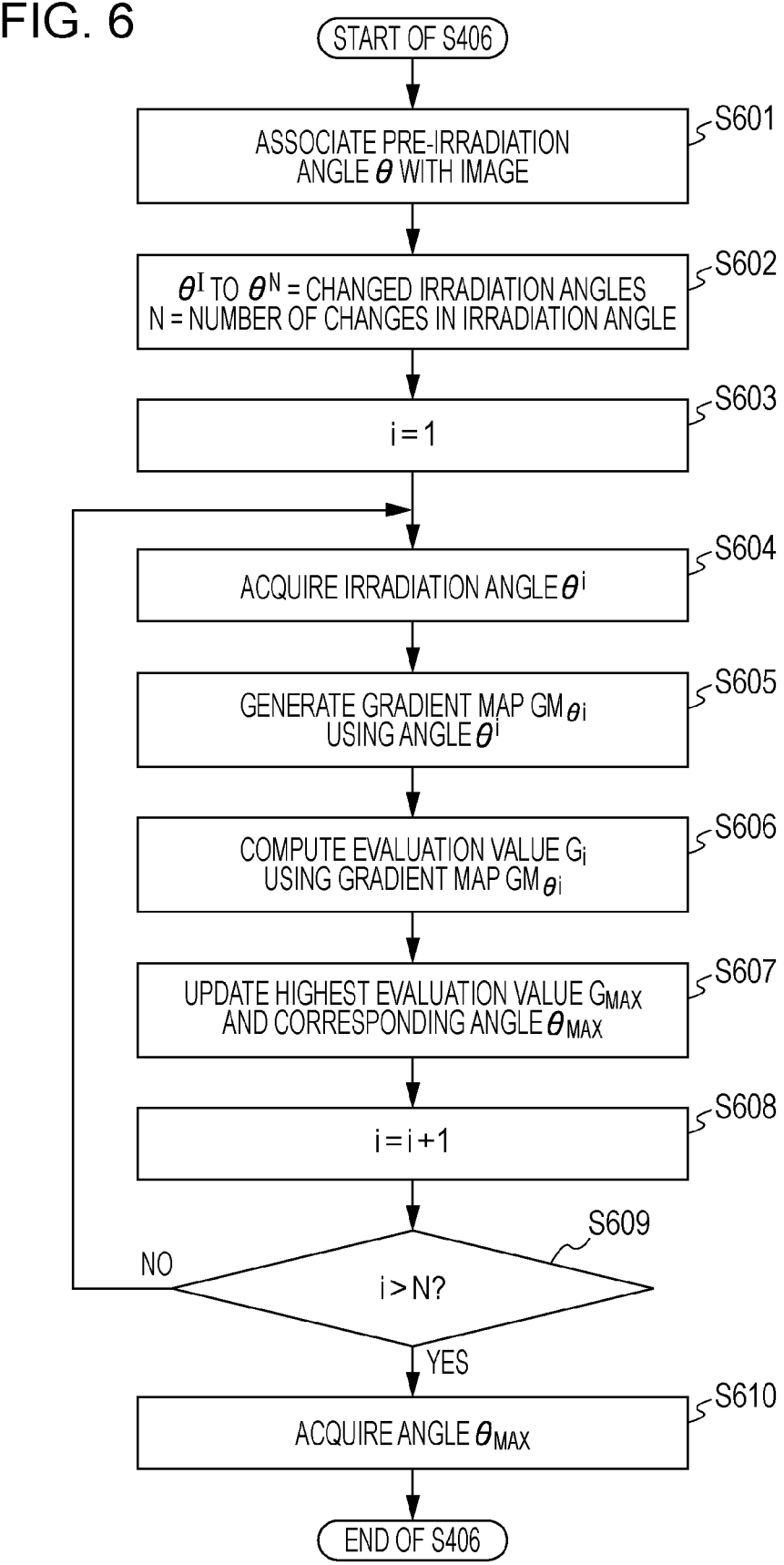
FIG. 6 is a flowchart of processing performed in step S406.
Figure 7:
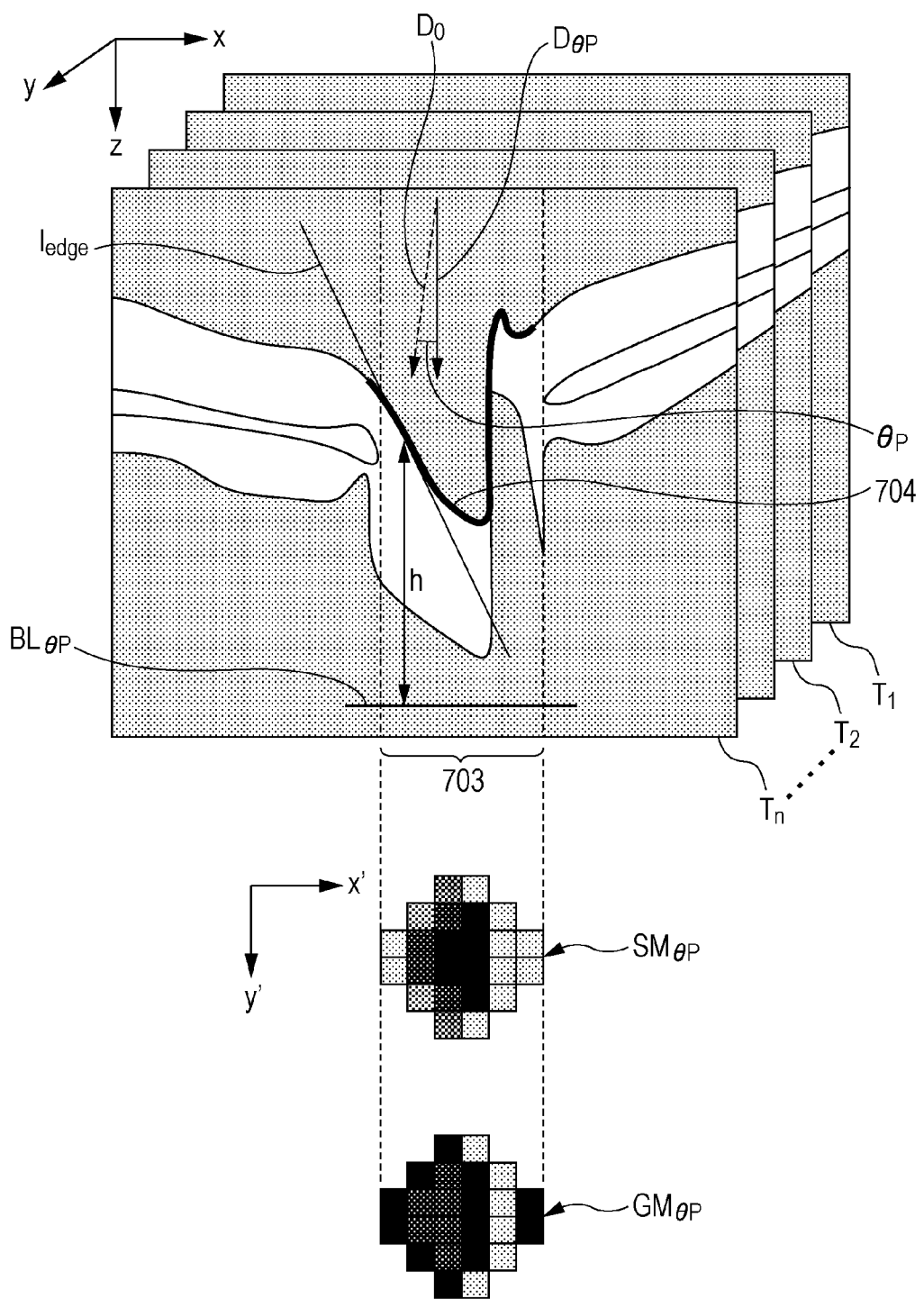
FIG. 7 is a gradient map regarding the optic papilla obtained by using pre-irradiation angle $\theta_{pre}$.
Figure 8:
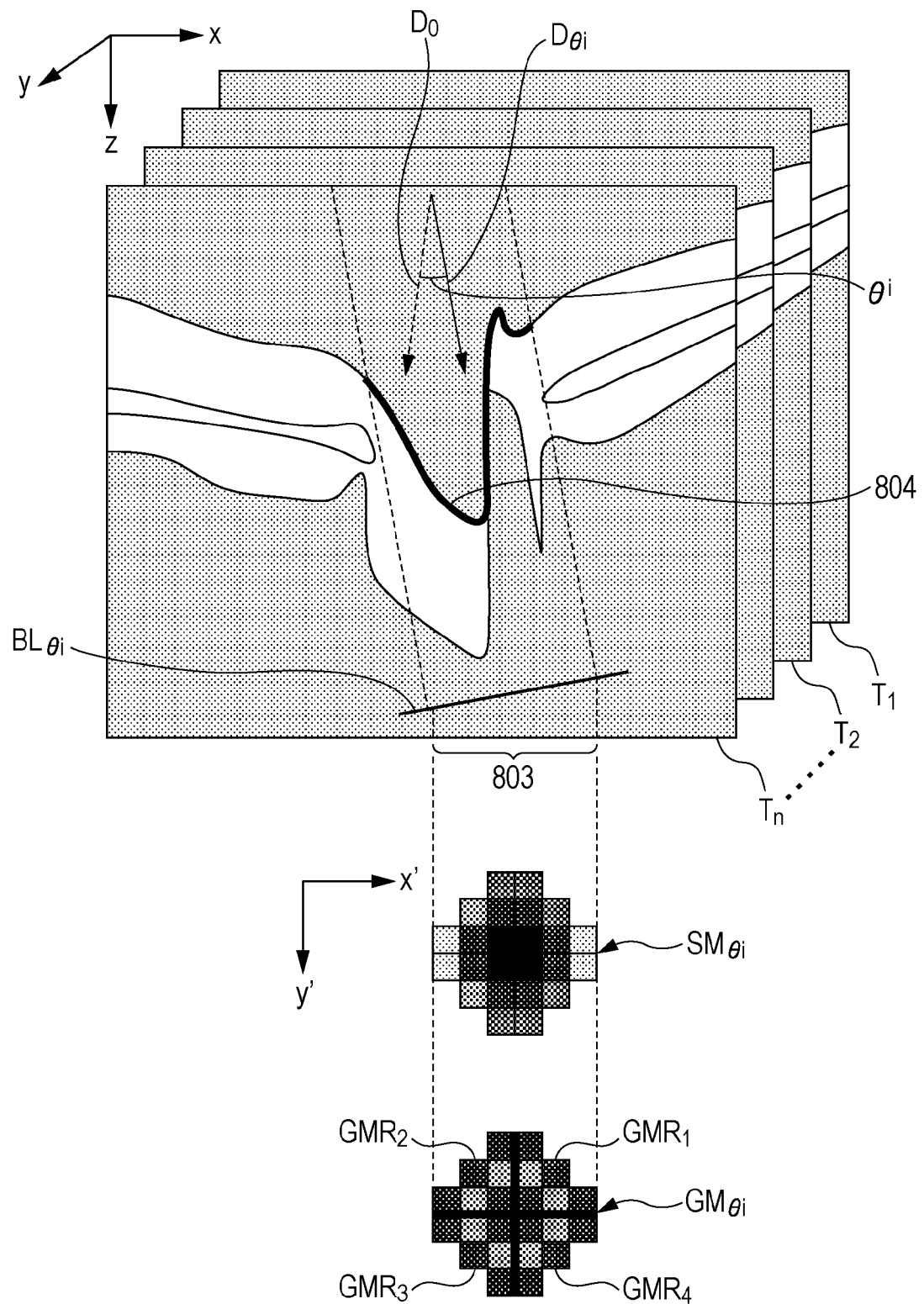
FIG. 8 is a gradient map in which the luminance distribution is made isotropic by controlling the irradiation angle.

FIG. 1 illustrates the configuration of an OCT imaging system according to the present embodiment. FIG. 2A illustrates a positional relationship between the pupil and the signal light beam. FIGS. 2B and 2C illustrate a relationship between the position of the signal light beam on the pupil and the irradiation angle of the signal light beam at a predetermined position. FIG. 3 is a functional block diagram of the OCT imaging system. FIG. 5 illustrates extraction of the shape of the surface of the optic papilla. FIG. 6 is a flowchart of processing performed by an information processing apparatus 102. FIG. 7 is a gradient map regarding the optic papilla obtained by using a pre-irradiation angle $\theta_{pre}$. FIG. 8 is a gradient map in which the luminance distribution is made isotropic by controlling the irradiation angle.

The configuration of the OCT imaging system is described next with reference to FIG. 1. In the OCT imaging system, an image capturing unit 101 receives an instruction to capture an image from the information processing apparatus 102. Thereafter, the OCT imaging system generates an interference light beam using a returning light beam of a signal light beam generated when the signal light beam emitted to an object to be imaged is reflected or scattered and a reference light beam and, subsequently, generates a tomographic image. As used herein, the term "returning light beam of the signal light beam" refers to a light beam generated when the signal light beam emitted to an object to be imaged is reflected or scattered by a predetermined layer or boundary surface and, subsequently, detected by the image capturing unit 101 in the form of a signal. The information processing apparatus 102 acquires the captured tomographic image, performs predetermined processing on the tomographic image, and displays the image on a display unit 103.

The configuration of the image capturing unit 101 is described next. The image capturing unit 101 serves as an optical coherence tomographic imaging apparatus using an optical interferometry imaging method. An image forming unit 104 uses instruction information received from the information processing apparatus 102 as an imaging parameter and controls a galvano mirror drive mechanism 105. Thus, the image forming unit 104 drives a galvano mirror 106. Thereafter, the image forming unit 104 splits, using a half mirror 108, a light beam emitted from a low-coherence source 107 into a signal light beam traveling towards an eye to be examined 110 via an objective lens 109 and a reference light beam traveling towards a reference mirror 111 fixedly disposed. Subsequently, the image forming unit 104 causes a returning light beam of the signal light beam reflected or scattered by the eye to be examined 110 to overlap with a returning light beam of the reference light beam reflected by the reference mirror 111 so as to generate an interference light beam. Note that in place of the half mirror 108, an optical coupler that functions as a splitter that splits a light beam and a coupler that causes light beams to overlap with each other may be employed. The interference light beam is separated into wavelength components of wavelengths $\lambda 1$ to $\lambda n$ using a diffraction grating 112. The wavelength components can be detected by a one-dimensional optical sensor array 113. Light sensors of the one-dimensional optical sensor array 113 outputs detection signals each corresponding to the intensity of a detected wavelength component to an image reconstruction unit 114. The image reconstruction unit 114 computes a wavelength—light intensity relationship for the interference light beam, that is, a light intensity distribution (a wavelength spectrum), using the detection signals for the wavelength components of the interference light beam output from the one-dimensional optical sensor array 113. The image reconstruction unit 114 performs Fourier transform on the computed wavelength spectrum of the interference light beam and reconstructs a tomographic image of the retina.

In addition, the image capturing unit 101 can change the incident angle of the signal light beam emitted to a tissue to be imaged. This operation is described in more detail below. A position control unit 116 uses the instruction information received from the information processing apparatus 102 as an imaging parameter and controls an image capturing unit drive mechanism 115. Thus, the position control unit 116 drives the image forming unit 104. More specifically, the instruction information indicates the incident position of the signal light beam made incident on the pupil of the eye to be examined in an x-y plane. The image capturing unit drive mechanism 115 translates the image forming unit 104 with respect to the eye to be examined 110 so that the signal light beam enters the incident position. Alternatively, the image capturing unit 101 itself may be translated. By controlling the position of the signal light beam made incident on the pupil relative to the center of the pupil in this manner, the irradiation angle of the signal light beam on the target tissue in the retina can be changed.

Figure 4:
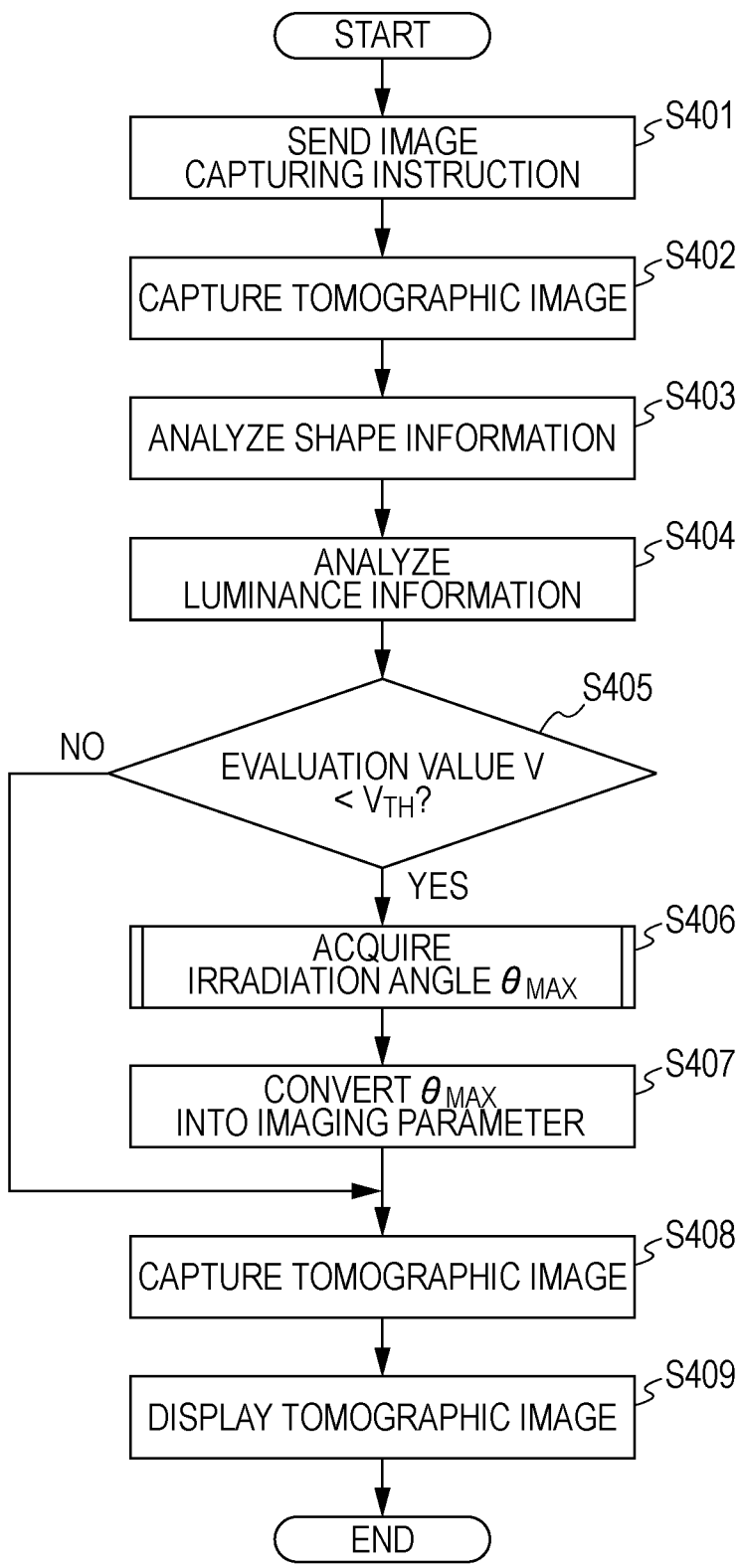
FIG. 4 is a flowchart illustrating the procedure of processing performed by an information processing apparatus 102 according to the first embodiment.

The configuration of the information processing apparatus 102 is described next. The information processing apparatus 102 sends information indicating a first irradiation angle to the image capturing unit 101 and instructs the image capturing unit 101 to capture an image. In addition, the information processing apparatus 102 sends, to the image capturing unit 101, information indicating a second irradiation angle obtained on the basis of a captured tomographic image and instructs the image capturing unit 101 to capture an image. The information processing apparatus 102 includes a CPU 118, a RAM 119, and a ROM 120, which are connected to one another via a bus 117. In addition, a mouse 121 serving as an input unit and an HDD 122 serving as a storage unit are connected to the information processing apparatus 102 via the bus 117. The ROM 120 stores a computer program that realizes processing shown in FIG. 7 described below. The program is loaded into the RAM 119 and is executed by the CPU 118. Thus, the program and each component of the information processing apparatus 102 cooperate with one another. As a result, the functions illustrated in FIG. 3 are realized. In addition, by performing the functions at the same time, the processing illustrated in FIGS. 4 and 7 is realized.

The irradiation angle of an irradiation light beam emitted from the image capturing unit 101 to the retina is described next with reference to FIGS. 2A to 2C. FIG. 2A is a schematic illustration of a positional relationship between the center of the pupil and the signal light beam made incident on the pupil.

In FIG. 2A, $E_1$ denotes the pupil, $P_0$ denotes the center of the pupil, and $IR_0$ denotes the center of an infrared image. The image of the pupil can be captured using, for example, an infrared camera. The image capturing unit 101 is pre-adjusted so that an incident position $P_L$ of the signal light beam emitted to the retina of the eye to be examined is aligned with the center of the pupil image. It is desirable that the incident position of the signal light beam be aligned with the center of the pupil. However, as in FIG. 2A, the irradiation position of the signal light beam may differ from the center of the pupil without precise positioning. In an infrared image, the contrast between the pupil area and the peripheral area increases. Accordingly, by detecting the image gradient, the contour of the pupil $E_1$ can be detected. The contour of the pupil $E_1$ can be approximated to a circle. Accordingly, the center of the approximated circle is denoted as the center of pupil P0, and the radius of the approximated circle is denoted as the radius of the pupil r. Thereafter, computation is performed. When the point $P_0$ represents an origin, the x-y coordinates of the point $P_L$ is denoted as $(x_L, y_L)$.

FIG. 2B illustrates a relationship between the signal light beam made incident on the pupil and the irradiation angle on the target tissue (the optic papilla). In FIG. 2B, $E_1$ denotes the pupil, $E_2$ denotes the cornea, $E_3$ denotes the eye ball, $E_4$ denotes the crystalline lens, MC denotes the macula, DC denotes the optic papilla, $P_0$ denotes the center of the pupil, $D_0$ denotes an irradiation direction of the signal light beam that passes through the center of the pupil $P_0$ and is emitted to the optic papilla DC, and $\theta_{LIM}$ denotes the limiting angle of the signal light beam. Hereinafter, $D_0$ denotes a "reference irradiation direction". Among signal light beams made incident on the pupil $E_1$, a signal light beam that is parallel to $D_0$ is refracted by $E_4$ due to the lens function of $E_4$ and is focused on DC. Accordingly, if the irradiation position of the signal light beam on the pupil is changed with the incident angle on the pupil remaining unchanged, the signal light beam is irradiated onto DC at an angle that varies in accordance with the irradiation position. At that time, the limiting angle $\theta_{LIM}$ of the signal light beam that can be physically changed with respect to the reference $D_0$ is an angle obtained when the signal light beam passes through the end of the pupil. In addition, the eye ball is an ellipsoidal body that is similar to a spherical body. Accordingly, when the eye ball is approximated by a spherical body, the cross section of $E_3$ is circular and, therefore, the limiting angle $\theta_{LIM}$ represents the angle at the circumference for the radius of the pupil. Consequently, according to the circumferential angle theorem, the value of $\theta_{LIM}$ is constant if the focal point of the signal light beam is set to any point on the retina. The same applies to the case when the focal point is set to MC. In such a case, since the line extending between $P_0$ and MC perpendicularly intersects with the pupil $E_1$, the $\theta_{LIM}$ can be obtained as follows:

[Math. 1]

$$\theta_{LIM} = \tan^{-1}\left(\frac{r}{l}\right) \quad (1)$$

where l denotes the length of a line extending between $P_0$ and MC. The length l may be measured by an axial length examination in advance or may be set to a widely used average value. More specifically, when the radius of the pupil r is 3 to 4 mm and the length of a line extending between $D_0$ and MC is 18.5 mm, $\theta_{LIM}$ is about 7.7° to about 10.7°.

In addition, in FIG. 2C, $E_1$, DC, $P_0$, $D_0$, and $\theta_{LIM}$ are the same as those in FIG. 2A. In addition, L denotes the central line of the signal light beam. $P_L$ denotes the position at which the signal light beam is made incident on $E_1$. $D_\theta$ denotes a direction in which the signal light beam that passes through the point $P_L$ and that is made incident on DC travels. $P_1$ denotes a reference point on the contour of $E_1$. Furthermore, $\theta_1$ denotes an angle formed by the line $P_0P_1$ and the line $P_0P_L$ on $E_1$, and $\theta_2$ denotes an angle formed by the line $P_0 \cdot P_1$ (the direction $D_0$) and the line $P_0 \cdot P_L$ (the direction $D_\theta$). At that time, the values of $\theta_1$ and $\theta_2$ are determined by the position of the point $P_L$. Thus, when the coordinates of the point $P_L$ is $(x_L, y_L)$, the values of $\theta_1$ and $\theta_2$ are obtained by using the following equations (2) and (3):

[Math. 2]

$$\theta_1 = \cos^{-1}\left(\frac{x_L}{\sqrt{x_L^2 + y_L^2}}\right) = \sin^{-1}\left(\frac{y_L}{\sqrt{x_L^2 + y_L^2}}\right) \quad (2)$$

$$\theta_2 = \tan^{-1}\left(\frac{\sqrt{x_L^2 + y_L^2}}{1}\right) \quad (3)$$

As in equation (1), in equation (3), $\theta_2$ is computed using an angle (an angle formed by the line $P_0 \cdot$MC and the line $P_L \cdot$MC) when the focal point of the signal light beam is set to MC. The irradiation angle including these angle components ($\theta_1$, $\theta_2$) is defined as "$\theta$".

In addition, by changing the incident position of the signal light beam on the pupil while keeping the incident direction on the pupil unchanged, the incident angle of the signal light beam on the retina can be changed while keeping the area of the retina which is irradiated with the signal light beam unchanged. Even when the image of a correct shape cannot be obtained when the signal light beam is emitted at the first angle, the image of the correct shape can be obtained by changing the incident angle to the second angle.

The function obtained from a combination of the software (the computer program) and the hardware of the information processing apparatus 102 is described next with reference to FIG. 3.

An image-capturing instruction unit 301 sends, to the image capturing unit 101, an instruction to capture the image of the retina at a predetermined irradiation angle. At that time, the sent information includes an image capturing condition, such as the irradiation angle. When the instruction to capture an image is received, the image capturing operation is started. First, the image-capturing instruction unit 301 performs a determination process of an irradiation angle, which is described in more detail below.

The tomographic image acquiring unit 302 acquires a tomographic image captured by the image capturing unit 101 using the imaging condition specified by the image-capturing instruction unit 301.

A shape analyzing unit 303 analyzes the layer structure of a tomographic image acquired by the tomographic image acquiring unit 302 and identifies the shape of the depressed part. The analysis of the layer structure is performed on the basis of the edges obtained from the luminance information on the tomographic image. A portion whose shape cannot be identified is estimated through an interpolation process. This processing is described in more detail below with reference to FIG. 5.

A re-image capturing determination unit 304 determines whether re-image capturing is necessary on the basis of the presence of a partial area of a depressed part that cannot be identified due to an insufficient amount of the returning light beam of the signal light beam reflected and scattered or the size of the partial area. The determination is made by separating the depressed part into small areas, obtaining the intensity of the returning light beam for each of the small areas, and detecting the small area having a signal intensity lower than a predetermined threshold value. If a detected area is found or if the area is larger than a predetermined value, the re-image capturing determination unit 304 determines that re-image capturing is necessary. This processing is described in more detail below with reference to FIG. 5.

If the re-image capturing determination unit 304 determines that re-image capturing is necessary, a re-image capturing angle determination unit 305 determines an irradiation angle at which the returning light beam emitted to the depressed part has a predetermined intensity on the basis of the shape of the depressed part, which is an object to be imaged. As used herein, the term "predetermined intensity" refers to the intensity of the returning light beam with which a shape analyzing unit 303 or a user can correctly identify the shape of the depressed part, that is, the intensity that minimizes the size of the area of the depressed part in which the intensity of the returning light beam of the signal light beam is lower than or equal to a reference value. The reference value is determined by using a shape analyzing algorithm used in the shape analyzing unit 303 or an algorithm selected by the user. The image-capturing instruction unit 301 instructs re-image capturing on the basis of the determined irradiation angle.

The display unit 103 displays a re-captured tomographic image. A storage unit 306 stores the re-image capturing information sent to the image capturing unit 101 and the captured tomographic images.

By employing such a structure, an irradiation angle that causes the intensity of a light beam emitted to the object to be imaged to be lower than or equal to a predetermined value can be determined in accordance with the result of shape analysis. Thereafter, an instruction to capture an image using the determined irradiation angle is sent. Accordingly, an area of the object to be imaged that does not appear in the captured image can be reduced. In addition, the shape of the depressed part, which is the object to be imaged, is analyzed using the tomographic image captured first, and it is determined whether re-image capturing is necessary or not on the basis of the result of the analysis. Thus, the number of unnecessary image capturing operations can be reduced.

The procedure of processing realized by each of the functions of the information processing apparatus 102 illustrated in FIGS. 2A to 2C is described next with reference to FIG. 4.
<Step S401>

In step S401, the image-capturing instruction unit 301 generates instruction information used for controlling a two-dimensional measurement area and a measurement depth for the eye fundus of the eye to be examined (hereinafter referred to as "instruction information 1"). For example, the instruction information 1 is given through user selection using the mouse 121. Alternatively, the information stored in the storage unit 306 may be used. In addition, the image-capturing instruction unit 301 generates instruction information used for controlling the irradiation position of the signal light beam on the pupil of the eye to be examined (hereinafter referred to as "instruction information 2"). The instruction information 2 represents an irradiation angle $\theta_{pre}$ which is an irradiation angle of the signal light beam on the retina of the eye to be examined. The image-capturing instruction unit 301 sends the instruction information 1 and the instruction information 2 to the image capturing unit 101. Note that $\theta_{pre}$ is not limited to any particular value. The irradiation angle $\theta_{pre}$ may have a predetermined value for the apparatus or a value that can be fine-tuned by an instruction from the user. That is, any $\theta_{pre}$ that allows the signal light beam to reach the retina in the eye fundus can be used.
<Step S402>

In step S402, upon receiving the instruction information 1 and 2, the image capturing unit 101 captures a tomographic image using the instruction information 1 and 2 received from the image-capturing instruction unit 301 as the imaging condition. The image capturing unit 101 instructs the position control unit 116 and the image capturing unit drive mechanism 115 to move the image forming unit 104 so that the signal light beam is made incident on the pupil at a position in accordance with the first irradiation angle $\theta_{pre}$. Image data I of the captured tomographic image and the value of the pre-irradiation angle $\theta_{pre}$ are stored in the storage unit 306.

Note that the instruction information 1 and 2 do not necessarily serve as a condition to start an image capturing operation. In such a case, the image-capturing instruction unit 301 may send the instruction information 1 and 2 to the image capturing unit 101 as the imaging condition and may send information indicating that image capturing is ready to the user. In this case, the user can start image capturing at a desired point in time.
<Step S403>

In step S403, the shape analyzing unit 303 acquires the image data I of the tomographic image stored in the storage unit 306 and extracts information on at least part of the surface shape of the optic papilla from the image data I. Here, the information on at least part of the surface is extracted, since the entirety of the shape need not be identified, but only identifying the correct shape or the structure is required in the processing according to the present embodiment. An image of the optic papilla is extracted in the form of the area of the boundary surface of the retina in which a pigment layer is not present (i.e., an inner limiting membrane).

The procedure of analyzing the surface shape of the optic papilla and the area in the vicinity of the surface in a tomographic image performed by the shape analyzing unit 303 is described next with reference to FIG. 5. As shown in FIG. 5, B-Scan images $T_1$ to $T_n$ are acquired. In the B-Scan images $T_1$ to $T_n$, an inner limiting membrane 501, a pigment layer of the retina 502, an optic papilla area 503, and an area 504 in which the intensity of the image signal is significantly low are shown. As a particular process of extracting the surface shape of the optic papilla, the shape of the inner limiting membrane 501, which is one of the boundary surfaces of a retina layer, is extracted first.

As shown in FIG. 5, the inner limiting membrane 501 is an upper boundary between the retina layer area (a white area in the drawing) and a background area (a gray area in the drawing). Since the inner limiting membrane 501 has a large luminance contrast difference, the inner limiting membrane 501 can be detected using the luminance contrast difference. For example, scanning is performed from a point having a z coordinate of zero for each A-scan line in the z-axis direction, and the scanning is stopped at a point at which the gradient of the luminance value of the image becomes higher or equal to a predetermined threshold value $Th_1$. In this way, a point of the inner limiting membrane 501 can be detected. When an A-scan line number is denoted as:

$i(1 \leq i \leq M$, where M denotes the number of A-scan lines), [Math. 3]

a point of the inner limiting membrane 501 corresponding to a line i is denoted as: $p_i$. At that time, the area 504 in which the intensity of the image signal is low has discontinuity of the retina layer area in the z-axis direction, and the z-axis coordinate between two neighboring points of the inner limiting membrane 501 significantly changes. In such a case, interpolation is performed between the two neighboring points using a line. In this example, linear interpolation is applied. In this way, interpolation can be performed on the area 504 using a straight line that is substantially parallel to the z-axis.

Subsequently, the shape of the pigment layer of the retina 502 is extracted. Since the pigment layer of the retina 502 is rendered in the retina layer area with particularly high luminance, the pigment layer of the retina 502 can be detected using the contrast in the retina layer. For example, for each A-scan line i, scanning is performed from a point $P_i$ in the z-axis direction, and the scanning is stopped at a point at which the gradient of the luminance value of the image becomes higher or equal to a predetermined threshold value $Th_2$ first. In this way, a point of the pigment layer of the retina 502 can be detected. Such a point is denoted as $q_i$. At that time, since the pigment layer of the retina 502 is not present in the optic papilla area 503, the coordinates of the point $q_i$ are set to a value F, which indicates "absence", if the point $q_i$ cannot be detected. Accordingly, the optic papilla area 503 can be detected as an area indicated by the x coordinate of the point $q_i$ having a value of F. Thereafter, the set of the points $P_i$ included in the detected optic papilla area 503 is obtained for each of $T_1$ to $T_n$. The sets are used as surface shape data S of the optic papilla.

<Step S404>

In step S404, the re-image capturing determination unit 304 determines whether re-image capturing is performed or not on the basis of the image data I and the surface shape data S acquired from the shape analyzing unit 303. This determination is made using the size of the area in which the intensity of a signal emitted to the depressed part or whether the area is present or not.

In FIG. 5, a retina layer area 505 in the vicinity of the inner limiting membrane 501 is shown. The retina layer area 505 is defined as an area included in a range within a predetermined distance d from every point of the surface shape data S (note that a background area above the inner limiting membrane 501 is not included). According to the present embodiment, the distance d is defined as a value obtained by dividing the average of the distances between the inner limiting membrane 501 and the pigment layer of the retina 502 for each of the A-scan lines by a constant value c (e.g., c=5).

Subsequently, the area 505 is separated into a plurality of local areas. In this example, the number of the local areas is k. The volume of the area 505 is evenly separated into areas $R_1$ to $R_K$. Thereafter, a luminance evaluation value $v_i$ is computed for each of the local areas $$R_i (1 \leq i \leq k) \quad \text{[Math. 4]}$$

using the following equation (4):

[Math. 5]

$$v_i = \frac{1}{m} \sum_{j=1}^{m} b_{(j)} \quad (4)$$

where m represents the number of pixels included in $R_i$, and $b_{(j)}$ represents the luminance of a jth pixel included in $R_i$ $$(1 \leq j \leq m) \quad \text{[Math. 6]}$$

In equation (4), the evaluation value $v_i$ represents the average of the pixel values of pixels included in the local area $R_i$. However, the evaluation value may be an S/N ratio computed using the following equation (5):

[Math. 7]

$$v_i = 20 \log_{10} \left\{ \frac{b'_{MAX}}{RMS^i} \right\} \quad (5)$$

where $b'_{max}$ represents the highest luminance value in $R_i$, and $RMS^i$ represents the RMS (Root Mean Square) computed in $R_i$. Furthermore, the luminance evaluation value V for the entirety of the area 505 is computed by using the following equation (6):

[Math. 8]

$$V = \min_{1 \leq i \leq k} \{v_i\} \quad (6)$$

In this way, by defining the lowest value of the luminance evaluation values $v_i$ computed for the local areas as the luminance evaluation value V for the entirety of the area 505, the evaluation value for the entirety of the area 505 can be obtained by taking into account the presence of an area in which the intensity of the image signal is locally low. Thereafter, the image data I and the luminance evaluation value V obtained through the analysis are sent to the re-image capturing determination unit 304.

It should be noted that the determination method is not limited thereto. For example, the evaluation may be made using the size of an area in which the shape of the depressed part cannot be identified through the analysis performed by the shape analyzing unit 303. In the above-described example, the luminance value of the depressed part is used. However, re-image capturing is not needed so long as the shape of the depressed part is identified. Accordingly, the number of unnecessary image capturing operations can be reduced. Similarly, the evaluation may be made using the size of an area to which linear interpolation is applied with respect to the shape of the depressed part or the size of an area having a shape that can be estimated through the analysis but that has a low reliability.

<Step S405>

In step S405, the re-image capturing determination unit 304 compares the luminance evaluation value V with a predetermined threshold value $V_{TH}$ and determines whether the tomographic image is displayed or not. If $V<V_{TH}$, the re-image capturing determination unit 304 sends, to the re-image capturing angle determination unit 305, an instruction to use an irradiation angle of the signal light beam at a predetermined position of the tissue to be imaged (hereinafter referred to as "instruction information 2"). Thereafter, the processing proceeds to step S406. However, if $V>=V_{TH}$, the re-image capturing determination unit 304 sends, to the display unit 103, the image data I and an instruction to permit displaying of the image data I (hereinafter referred to as "instruction information 1"). Thereafter, the processing proceeds to step S407. Note that the size of an area in which the intensity of the image signal is low may be used as the evaluation value. In such a case, determination of whether re-image capturing is performed is made by changing the threshold value for the size. Thus, the balance between the period of time required for re-image capturing and the correctness of the image information that can be obtained through the re-image capturing can be determined.

<Step S406>

In step S406, upon receiving the instruction information 2 from the re-image capturing determination unit 304, the re-image capturing angle determination unit 305 acquires, from the storage unit 306, the pre-irradiation angle $\theta_{pre}$ used when the tomographic image is captured in step S402. Thereafter, the re-image capturing angle determination unit 305 acquires a second irradiation angle $\theta_{MAX}$ at which the intensity of the returning light beam of the signal light beam is equal to a desired intensity in the depressed part, which is an object to be imaged, in accordance with the pre-irradiation angle $\theta_{pre}$ (the first irradiation angle) and the image data I and the surface shape data S acquired from the shape analyzing unit 303. Subsequently, an incident position $P_L$: $(x_L, y_L)$ of the signal light beam in the pupil of the eye to be examined is computed using the acquired irradiation angle $\theta_{MAX}$. The re-image capturing angle determination unit 305 then sends the incident position $P_L$ to the image capturing unit 101 as instruction information 3. In this example, an irradiation angle at which the surface area of the optic papilla to which the signal light beam is not emitted (or the surface area having a significantly low intensity of a reflected light beam obtained from the eye to be examined after the light beam is emitted) is minimized is denoted as $\theta_{MAX}$. This processing is described in more detail below with reference to a flowchart shown in FIG. 7.

<Step S407>

In step S407, the re-image capturing angle determination unit 305 converts the irradiation angle $\theta_{MAX}$ obtained in step S406 into an imaging parameter. More specifically, the reverse of the process in which the point $P_L(x_L, Y_L)$ on the retina at which the signal light beam is made incident is converted into an irradiation angle $\theta$: $(\theta_1, \theta_2)$ as illustrated in step S402 is performed. That is, an angle $\theta$ is converted into the point $P_L$. This conversion is performed using the following equations (7) and (8):

[Math. 9]

$$x_L = (l \tan \theta_2) \cos \theta_1 \qquad (7)$$

$$y_L = (l \tan \theta_2) \sin \theta_1 \qquad (8)$$

where, as in step S402, r represents the radius of a pupil, and l represents a line $P_0 \cdot MC$. The image-capturing instruction unit 301 sends the coordinates of the point $P_L$ computed in the above-described manner to the image capturing unit 101 as the instruction information 2.

<Step S408>

In step S408, the image capturing unit 101 captures a tomographic image using the instruction information 2 acquired from the re-image capturing angle determination unit 305 as an imaging parameter and acquires the image data I of the tomographic image. At that time, an imaging method that is the same as that used in step S402 is employed. In order to change the irradiation angle of the signal light beam on the target tissue from the first irradiation angle $\theta_{PRE}$ to the second irradiation angle $\theta_{MAX}$, the image forming unit 104 is moved using the position control unit 116 and the image capturing unit drive mechanism 115. However, a method for changing the irradiation angle is not limited thereto. For example, the position of a fixation lamp that is presented to the eye to be examined may be changed. Thereafter, the incident position of the signal light beam on the pupil may be changed by rotating the eye to be examined while the eye fixates that position. In such a case, the configuration of the apparatus can be advantageously simplified. Subsequently, the image capturing unit 101 sends the image data I of the tomographic image and the instruction information 1 to permit displaying of the image data I to the display unit 103.

<Step S409>

In step S409, upon receiving the instruction information 1 from the re-image capturing determination unit 304 or the image capturing unit 101, the display unit 103 displays the image data I acquired in a similar manner.

According to the above-described configuration, the shape of the depressed part of the optic papilla is analyzed from the three-dimensional tomographic image of the optic papilla captured using the first irradiation angle $\theta_{PRE}$. Thereafter, the second irradiation angle $\theta_{MAX}$ at which an area in which the intensity of the signal light beam emitted to the depressed part is lower than or equal to a reference value is minimized is determined using the result of the analysis, and a tomographic image is captured again. In this way, a tomographic image in which the depressed part is sufficiently rendered can be obtained. In addition, since an optimal irradiation angle can be automatically acquired, the photographer need not manually control the irradiation angle and, therefore, the time required for controlling the irradiation angle can be reduced. Furthermore, a photographer-to-photographer variation in control of the irradiation angle can be eliminated.

The process performed by the re-image capturing angle determination unit 305 acquiring the irradiation angle $\theta_{MAX}$ in step S406 is described in more detail next with reference to a flowchart in FIG. 6. In this process, the irradiation angle is changed using simulation, and the intensity of the signal light beam at each point of the depressed part is obtained for each of the irradiation angles. Thus, an angle at which an area in which the intensity is lower than a predetermined threshold value is minimized is obtained as $\theta_{MAX}$. The intensity of the signal light beam at each point of the depressed part is obtained by computing an angle formed by the signal light beam and the gradient regarding the shape at each point of the depressed part.

<Step S601>

In step S601, the re-image capturing angle determination unit 305 acquires the pre-irradiation angle $\theta_{PRE}$ from the storage unit 306 and associates the reference irradiation direction $D_0$ with the image data I of the tomographic image.

<Step S602>

In step S602, the re-image capturing angle determination unit 305 defines the number of changes in irradiation angle as N and determines changed irradiation angles $\theta^1$ to $\theta^N$ using the reference irradiation direction $D_0$ as a reference. Thereafter, the re-image capturing angle determination unit 305 stores these values in the storage unit 306. An angle component $(\theta_1, \theta_2)$ of $\theta$ satisfies the following conditions:

$$0° \leq \theta_1 \leq 360°, \ 0° \leq \theta_2 \leq \theta_{LIM} \qquad \text{[Math. 10]}$$

Accordingly, the angle $\theta_1$ ranging from 0° to 360° is divided into $N_1$ equal angles, which are sequentially denoted as $\theta_1^1, \ldots \theta_1^j, \ldots, \theta_1^{N1}$. Similarly, the angle $\theta_2$ ranging from 0° to $\theta_{LIM}$ is divided into $N_2$ equal angles, which are sequentially denoted as $\theta_2^1, \ldots \theta_2^k, \ldots, \theta_2^{N2}$ where $$1 \leq j \leq N_1, \ 1 \leq k \leq N_2 \qquad \text{[Math. 11]}$$

In addition, the changed irradiation angles $\theta^1$ to $\theta^N$ are sequentially set a number of times equal to the number of combination of $(\theta_1^j, \theta_2^k)$. Thus, the number of changes $N=N_1 \cdot N_2$.

<Step S603>

In step S603, the re-image capturing angle determination unit 305 defines a process number used for changing the irradiation angle as:

$$i \ (1 \leq i \leq N) \qquad \text{[Math. 12]}$$

Then, the re-image capturing angle determination unit 305 sets i to 1 and acquires the surface shape data S.

<Step S604>

In step S604, the re-image capturing angle determination unit 305 acquires an irradiation angle $\theta^i$ from the storage unit 306.

<Step S605>

In step S605, the re-image capturing angle determination unit 305 analyzes, using the irradiation angle $\theta^i$, the gradient information of the surface shape data S acquired in a similar manner. Thus, the re-image capturing angle determination unit 305 generates a gradient map $GM_{\theta i}$ of the surface shape data S. The gradient map indicates an angle formed by the emitted signal light beam and the gradient of each of the points of the depressed part.

The reason why the gradient map is generated is described next. The surface area of the optic papilla is rendered in a tomographic image with a higher luminance as the intensity of a light beam of the signal light beam that is reflected by each of the local areas of the surface and passes through the pupil increases. In addition, the intensity of the reflected light beam of each of the local areas increases as the signal light beam is emitted to the surface of the local area at an angle closer to a right angle, since a difference between the irradiation angle of the light beam and the reflected light beam decreases. This relationship is described from another point of view with reference to FIG. 7.

In FIG. 7, $I_{edge}$ represents the tangent line of a local area on the surface shape data S. $BL_{\theta p}$ represents a plane that is perpendicular to the irradiation direction of the signal light beam ($D_{\theta p}$ in this drawing). This plane is defined as a projection reference plane of the signal light beam. In addition, h represents the height of the local area from the projection reference plane. At that time, as the gradient of the tangent line $I_{edge}$ with respect to the projection reference plane $BL_{\theta p}$ decreases, $I_{edge}$ is closer to a direction perpendicular to the irradiation direction. Thus, the intensity of the light beam reflected by the local area increases. In addition, the gradient of the tangent line $I_{edge}$ is the same as a change in the height h of the local area with respect to the projection reference plane, that is, the shape gradient. As a result, as the shape gradient of the local area with respect to the projection reference plane decreases, the intensity of the image signal obtained when the area is imaged increases. For the above-described reason, according to the present embodiment, a gradient map including the gradient value of each of the local areas is generated, and the gradient map serves as an index used for estimating how the entirety of the surface shape of the optic papilla is imaged when the signal light beam is emitted to the optic papilla in a certain irradiation direction.

An example of a method for generating the gradient map $GM_{\theta i}$ is described next. The above-described projection reference plane is separated into a plurality of local areas. In this example, the local areas are rectangular areas $A_j$ having the same dimensions. Thus, the projection reference plane is separated into areas $A_1$ to $A_{NA}$ ($1 \leq j \leq N_A$, where NA denotes the number of separated areas)     [Math. 13]

Let $B_j$ denote an area on the surface shape data S corresponding to the area $A_j$ on the projection reference plane when the surface shape data S is projected onto the projection reference plane, and $h_j$ denote the height of the area $B_j$ with respect to the projection reference plane. Then, a map including $h_j$ as the luminance value of each of the areas $A_j$ is generated. This map is referred to as a "shape map". Subsequently, a luminance gradient $g_j$ of each of the luminance values $h_j$ of the shape map is computed. According to the present embodiment, $g_j$ is computed using a Sobel filter. Thereafter, a map including the computed $g_j$ as the luminance value of the area $A_j$ is generated. This map is referred to as a "gradient map". In this way, the angle of the gradient of each of the points of the depressed part with respect to the signal light beam can be obtained.

FIG. 7 illustrates a gradient map of the optic papilla at the pre-irradiation angle $\theta_{pre}$ (described in more detail below). In FIG. 7, the direction $D_0$ and an irradiation direction $D_{\theta p}$ of the signal light beam emitted at the pre-irradiation angle $\theta_{pre}$ are shown. Since the image data I represents an image captured using the signal light beam at the irradiation angle $\theta_{pre}$, $D_{\theta p}$ is the same as the z-axis direction. Accordingly, the reference irradiation direction $D_0$ represents a direction tilted at an angle of $\theta_{pre}$ with respect to the z-axis in the image. In practice, the angle $\theta_{pre}$ has components $(\theta_1, \theta_2)$ and is three-dimensional. However, for simplicity, the angle $\theta_{pre}$ is expressed as an angle projected to a two-dimensional plane in FIG. 7.

In FIG. 7, tomographic images $T_1$ to $T_n$ and an optic papilla area 703 are shown. Furthermore, in particular, an inner limiting membrane 704 of the optic papilla area 703 is shown. Note that the inner limiting membrane 704 corresponds to the surface shape data S. Still furthermore, a shape map $SM_{\theta p}$ of the inner limiting membrane 704 in which the height h is expressed for each of the areas and a gradient map $GM_{\theta p}$ of the inner limiting membrane 704 that includes the differential values of the shape map $SM_{\theta p}$ are shown. The gradient map $GM_{\theta p}$ indicates the incident angle of the signal light beam on each of the partial areas of the depressed part. Accordingly, the gradient map $GM_{\theta p}$ indicates the intensity of the signal light beam in each of the partial areas.

x' and y' represent the coordinate axes in $SM_{\theta p}$ and $GM_{\theta p}$. In the shape map $SM_{\theta p}$, a change in luminance is gentle from the center of the map in the negative x' axis direction. However, a change in luminance is abrupt from the center of the map in the positive x' axis direction. Accordingly, in the gradient map $GM_{\theta p}$, an area in which the luminance is significantly high appears on the right side from the center of the map. This area corresponds to part of the inner limiting membrane 704 having a shape gradient that is substantially parallel to the irradiation direction $D_{\theta p}$.

By replacing the angles $\theta_p$, $BL_{\theta p}$, $SM_{\theta p}$, and $GM_{\theta p}$ with $\theta^i$, $BL_{\theta i}$, $SM_{\theta i}$, and $GM_{\theta i}$ in FIG. 7, respectively, the gradient map $GM_{\theta i}$ corresponding to the irradiation angle $\theta^i$ can be obtained.

<Step S606>

In step S606, the re-image capturing angle determination unit 305 computes a gradient evaluation value $G_i$ on the basis of the generated gradient map $GM_{\theta i}$. This evaluation value indicates the size of an area of the depressed part in which the signal intensity at each point is lower than or equal to a predetermined threshold value. The number of the areas in which the average of the gradients obtained in step S605 is smaller than or equal to a predetermined threshold value is defined as the gradient evaluation value $G_i$. Alternatively, in the partial areas in which the inverse number of the gradient is higher than or equal to a predetermined threshold value, the inverse numbers of all of the areas may be summed. The sum may be used as the gradient evaluation value $G_i$. In such a case, the predetermined threshold value may be set in advance or may be specified by the user. Thus, the predetermined threshold value may be changed on the basis of the shape analyzing algorithm or a user requirement.

According to the present embodiment, the following evaluation value is employed as one of the evaluation values $G_i$ that minimizes the surface area of the optic papilla to which the signal light beam is not emitted. That is, let $g_i$ denote the gradient value of each of the above-described local areas on the gradient map $GM_{\theta i}$, and $g_{TH}$ denote a constant gradient threshold value. Then, the evaluation values $G_i$ is computed using the following equations (9) and (10):

[Math. 14]

$$g'_j = \begin{cases} 0 & (g_j \geq g_{TH}) \\ g_{TH} - g_j & (0 \leq g_j \leq g_{TH}) \end{cases} \quad (9)$$

$$G_i = \frac{1}{1 + \sum_{j=1}^{N_A} g'_j} \quad (10)$$

According to equation (10), as the number of the local areas having the gradient value lower than or equal to $g_{TH}$ decreases and a difference between the gradient value smaller than $g_{TH}$ and $g_{TH}$ decreases, $G_i$ increases. Under the opposite condition, $G_i$ decreases.

FIG. 8 illustrates a gradient map obtained when the signal light beam is uniformly emitted to the optic papilla. In FIG. 8, reference numerals $T_1$ to $T_n$, 803, 804, and $D_0$ are the same as those in FIG. 7. $D_{\theta i}$ denotes an irradiation direction of the signal light beam emitted at the irradiation angle $\theta_i$. $BL_{\theta i}$ denotes the projection reference plane corresponding to the irradiation angle $\theta_i$. h denotes the height of an inner limiting membrane 804 with respect to the projection reference plane $BL_{\theta i}$. $SM_{\theta i}$ denotes the shape map of the inner limiting membrane 804. $GM_{\theta i}$ denotes the gradient map of the inner limiting membrane 804. In FIG. 8, for the irradiation directions $D_{\theta i}$, the signal light beam is emitted in an isotropic manner throughout the inner limiting membrane 804 when viewed from the middle of the inner limiting membrane 804. Accordingly, the gradient map $GM_{\theta i}$ indicates a luminance distribution with a small number of local areas having a significantly small gradient value. Therefore, in this case, the evaluation value $G_i$ increases. In contrast, if the signal light beam is emitted in a significantly limited range of direction, the number of local areas having a significantly small gradient value increases. Thus, the evaluation value $G_i$ decreases.

<Step S607>

In step S607, if the highest evaluation value $G_{MAX}$ is not stored in the storage unit 306, the re-image capturing angle determination unit 305 performs setting so that $G_{MAX}=G_i$ and stores $G_{MAX}$ in the storage unit 306. However, if the highest evaluation value $G_{MAX}$ has already been stored in the storage unit 306, the re-image capturing angle determination unit 305 compares $G_{MAX}$ with $G_i$. If $G_{MAX}<G_i$, the re-image capturing angle determination unit 305 updates $G_{MAX}$ so that $G_{MAX}=G_i$ and stores $G_{MAX}$ in the storage unit 306. In addition, the re-image capturing angle determination unit 305 updates the irradiation angle $\theta_{MAX}$ corresponding to $G_{MAX}$ so that $\theta_{MAX}=\theta_i$ and stores $\theta_{MAX}$ in the storage unit 306.

<Step S608>

In step S608, the re-image capturing angle determination unit 305 increments the process number i by one.

<Step S609>

In step S609, the re-image capturing angle determination unit 305 compares the process number i with the number of changes N. If i>N, the processing proceeds to step S608. Otherwise, the processing proceeds to step S903.

<Step S610>

In step S608, the re-image capturing angle determination unit 305 acquires the irradiation angle $\theta_{MAX}$ from the storage unit 306. At that time, the re-image capturing angle determination unit 305 performs setting so that $\theta_{MAX}=\{\theta_{M1}, \theta_{M2}\}$. Thereafter, the processing returns to step S406, where a termination process is performed.

By finding the highest value of the gradient evaluation value $G_i$ through trial and error changing the irradiation angle through the above-described processing, the optimal irradiation angle $\theta_{MAX}$ can be obtained.

Modification 1

A modification of the gradient evaluation value $G_i$ is described next. In particular, this is suitable for a normal depressed part having an uncurved depression. In particular, this gradient evaluation value is suitable for a normal depressed part having an uncurved depression. The term "uncurved depression" refers to depression having the center axis thereof that is substantially straight. In such a case, the irradiation angle that causes the signal light beam to be parallel to the center axis of the depression serves as $\theta_{MAX}$. In addition, the property in which the signal intensity is isotropic with respect to the center axis of the depression is used. FIG. 8 illustrates the case in which the signal light beam is emitted to a depressed part without a complicated shape, such as curvature, at an appropriate irradiation angle. In such a case, the intensity of the signal light beam emitted to the depressed part of the inner limiting membrane 804 is isotropic and, therefore, the gradient map $GM_{\theta i}$ indicates a luminance distribution having an equal luminance area expanding from the center of the map in a ring shape. In this case, areas $GMR_1$ to $GMR_4$ have a similar luminance distribution.

Let $r_1$ to $r_4$ denote the average luminance values of the $GMR_1$ to $GMR_4$, respectively. Let the following notation represent the variance:

$r_j (1 \leq j \leq 4)$ [Math. 15]

Then, the evaluation value $G_i$ can be expressed as the inverse number of the variance using the following equation (11):

[Math. 16]

$$G_i = \frac{1}{\sum_{j=1}^{n} (r_{avg} - r_j)^2} \quad (11)$$

where $r_{avg}$ represents the average value of up to $r_1$ to $r_4$. As indicated by equation (11), $G_i$ increases as the values $r_1$ to $r_4$ are equalized among the areas $GMR_1$ to $GMR_4$. In contrast, $G_i$ decreases as the values $r_1$ to $r_4$ more significantly vary.

When, as shown in FIG. 8, the irradiation angle $\theta^i$ is isotropic with respect to the center of the depressed part throughout the shape data S, the value increases. If it is estimated that the depressed part is not curved, the evaluation value according to the present modification can be used.

Modification 2

According to a second modification, a second irradiation angle is computed so that the signal intensity becomes the highest for an area in which the signal intensity is small in a first tomographic image. In this case, the shape of the depressed part can be correctly identified by causing the display unit 103 to display a first tomographic image captured using the first irradiation angle and a second tomographic image captured using the second irradiation angle. In addition, the tomographic images may be combined using the configuration of a third embodiment described below. In such a case, a tomographic image that represents a more correct shape can be obtained. More specifically, the gradient evaluation value computed by the re-image capturing angle determination unit 305 in step S606 described above can be used as a high evaluation value when the highest amount of light is emitted to an area that has been subjected to interpolation since the shape in the tomographic image captured using the first irradiation angle $\theta_{PRE}$ has not been correctly identified.

Modification 3

In addition, in the first embodiment, the irradiation angle of the signal light beam is computed so that the gradient values of the surface shape of the optic papilla is isotropic throughout the surface shape. However, a method for analyzing the surface shape is not limited thereto. For example, the surface shape is analyzed using the following method, and the irradiation angle $\theta_{MAX}$ is computed. The method is described with reference to FIG. 7. The deepest position in the depressed part is detected using the surface shape data S acquired by the shape analyzing unit 303 according to the first embodiment. This position is denoted as a point "$p_D$". An area corresponding to the optic papilla area 703 in a projection reference surface T' in the shape map is denoted as "703", and a point corresponding to the point $p_D$ is denoted as a "point $P_D$'". Then, an irradiation angle θ at which the point $P_D$' is aligned with the median point of the area 703' is obtained as $\theta_{MAX}$. In this way, an irradiation angle at which the deepest point of the depression is set at the center of the optic papilla area can be obtained. By using this method, the irradiation angle can be obtained through further simplified image analysis.

While the first embodiment and the modifications of the first embodiment have been described with reference to a method for identifying the shape of the depressed part from a tomographic image captured by an OCT imaging apparatus, the present invention can be applied using a method other than the above-described method.

Second Embodiment

According to a second embodiment, a plurality of tomographic images are captured using different irradiation angles in advance, and the tomographic images are analyzed. Thus, one of the tomographic images in which the tissue of the depressed part is rendered best is selected and displayed.

More specifically, one of a plurality of tomographic images captured in the following manner is selected. A plurality of tomographic images are captured using the signal light beams emitted at different angles. A three-dimensional surface shape of the optic papilla is extracted from each of the tomographic images. Thereafter, the intensity of an image signal in an interior region in the vicinity of the optic papilla is computed using the three-dimensional surface shape. The intensity of an image signal is computed using a method that is the same as that of the first embodiment. The tomographic image corresponding to the interior region having the highest image signal is selected and displayed. This is because as the intensity of the signal light beam reaching the depressed part increases, the signal appearing in the image increases. Accordingly, unlike the case in which an optimal angle is selected from among the possible irradiation angles and an image is captured, if it is desirable that a tomographic image is captured using an irradiation angle at which the tissue of the depressed part is roughly imaged, the processing time required for image analysis can be reduced by reducing the number of imaging operations. Thus, the object can be achieved in a simplified manner.

Figure 9:
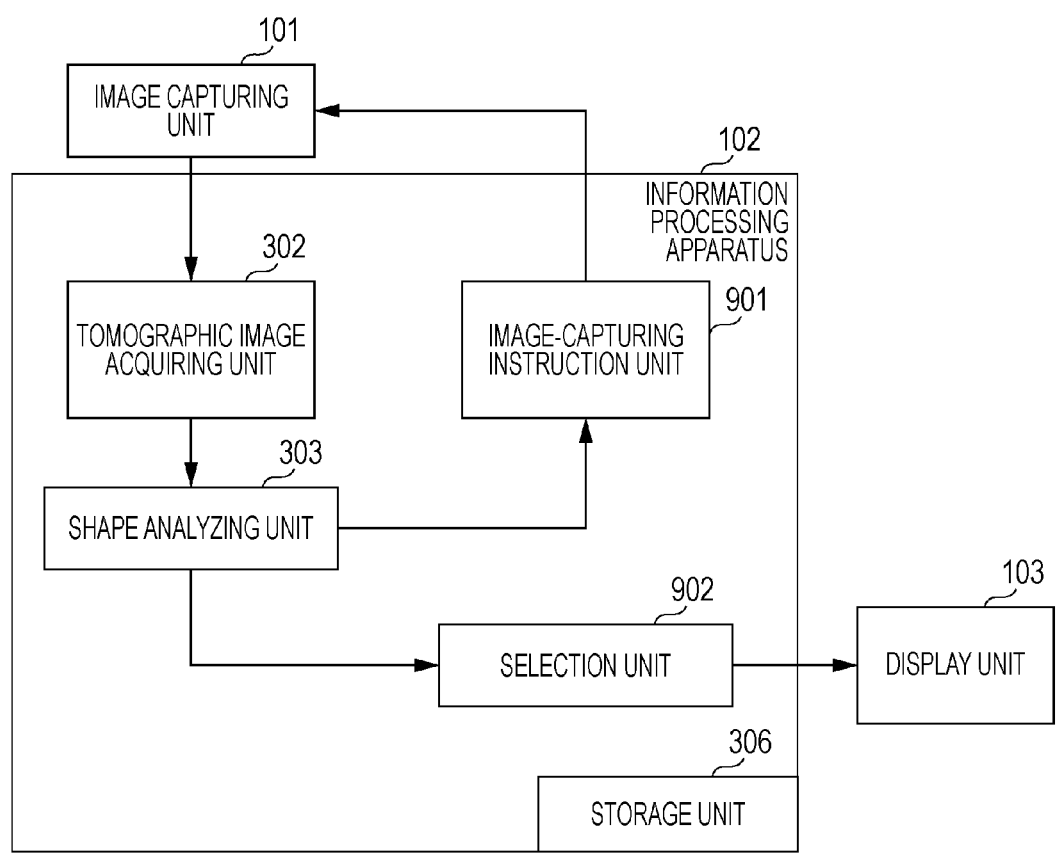
FIG. 9 is a functional block diagram of an OCT imaging apparatus according to a second embodiment.

FIG. 9 is a functional block diagram of an information processing apparatus 102 according to the present embodiment. The functions the same as those of the first embodiment are denoted by the same reference numerals, and the descriptions thereof are not repeated.

An image-capturing instruction unit 901 presets a plurality of irradiation angles of the signal light beam emitted to the depressed part of the retina. Thereafter, the image-capturing instruction unit 901 sends, to an image capturing unit 101, conditions including the preset irradiation angles and instructs the image capturing unit 101 to capture an image.

From among the captured tomographic images, a selection unit 902 selects the tomographic image in which the number of local areas in the depressed part having a signal intensity lower than or equal to a predetermined threshold value is small. In this way, an image that most adequately represents the shape of the depressed part can be selected. The selection unit 902 instructs the display unit 103 to display the selected image.

Figure 10:
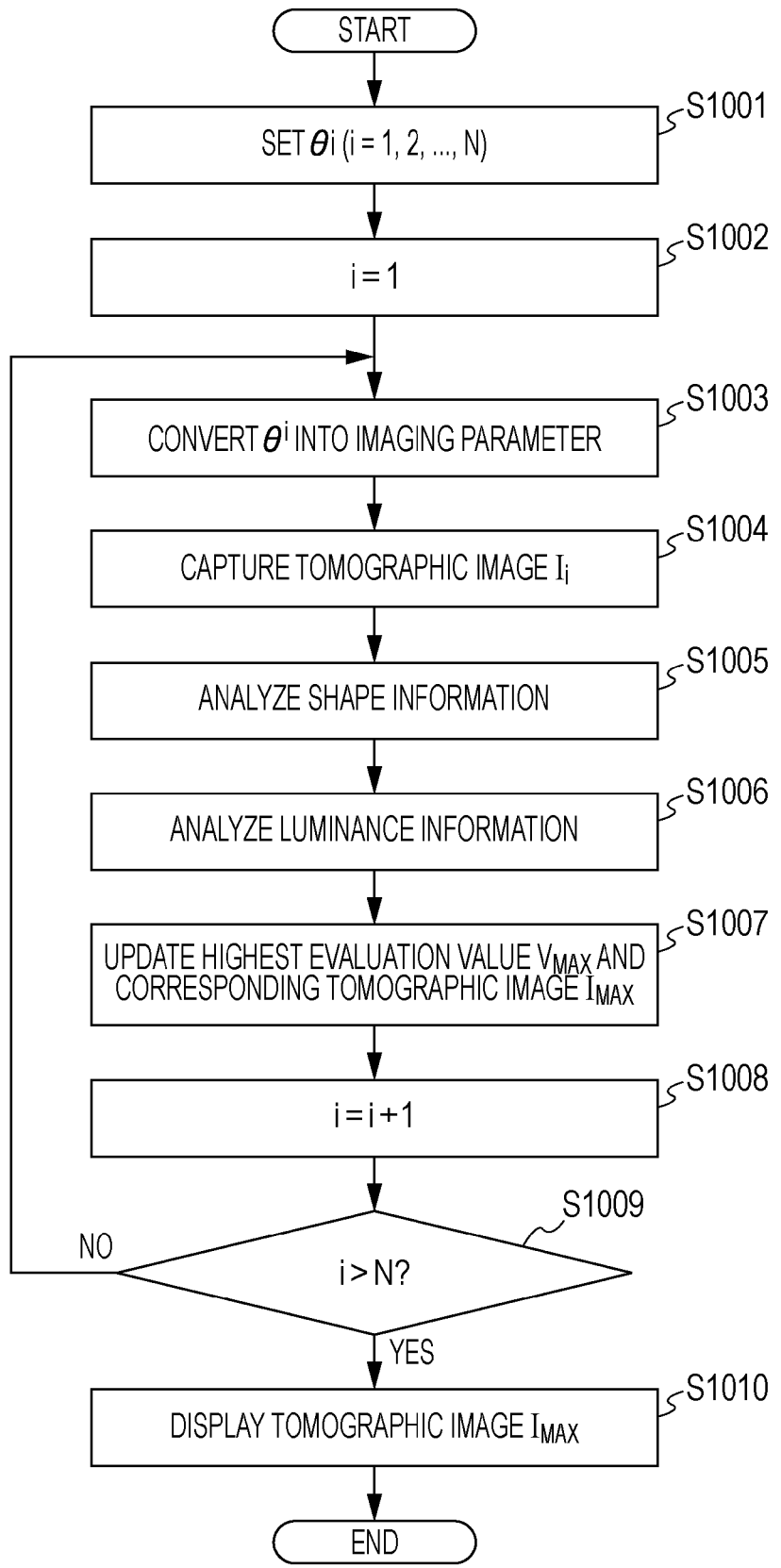
FIG. 10 is a flowchart illustrating the procedure of processing performed by an information processing apparatus 102 according to the second embodiment.

A particular processing procedure performed by an image-capturing support unit 130 according to the present embodiment is described next with reference to FIG. 10.

<Step S1001>

In step S1001, the image-capturing instruction unit 901 generates the instruction information 1. In addition, the image-capturing instruction unit 901 sets the number of changes in an irradiation angle to N, sets irradiation angles $\theta^1$ to $\theta^N$, and stores the set irradiation angles. At that time, the irradiation angles $\theta^1$ to $\theta^N$ are set using the method employed in step S602 in the first embodiment. Note that, in step S602, $\theta^1$ to $\theta^N$ are exhaustively set in the possible range. However, in this case, the intervals of the angle may be set more coarsely. This is because, unlike the case of the first embodiment in which an optimal irradiation angle is searched for, only a tomographic image in which the tissue of the depressed part is roughly imaged is required in this case. For example, for the angle component $\theta_1$ of the angle θ, a division number $N_1=4$ ($\theta_1$ in the range from 0° to 360° is divided into four equal angles). In addition, for the angle component $\theta_2$ of the angle θ, a division number $N_2$ is set as follow:

$$N_2=2(0° \leq \theta_2 \leq \theta_{LIM} \text{ is divided into two equal angles}) \quad [\text{Math. 17}]$$

The combinations for N=8 is sequentially denoted as $\theta^1$ to $\theta^8$.

Subsequently, the image-capturing instruction unit 901 sends the instruction information 1 to the image capturing unit 101.

<Step S1002>

In step S1002, the image-capturing instruction unit 301 defines a process number used when the irradiation angle is changed as follows:

$$i(1 \leq i \leq N) \quad [\text{Math. 18}]$$

Thereafter, the image-capturing instruction unit 301 performs setting so that i=1.

<Step S1003>

In step S1003, the image-capturing instruction unit 301 converts the irradiation angle $\theta^i$ to an imaging parameter and defines the imaging parameter as instruction information 2. Thereafter, the image-capturing instruction unit 301 sends the instruction information 2 to the image capturing unit 101. A conversion method is the same as that employed in step S407 shown in FIG. 4 and, therefore, the description thereof is not repeated.

<Step S1004>

In step S1004, the image capturing unit 101 captures a tomographic image using the instruction information 1 and the instruction information 2 received from the image-capturing instruction unit 301 as the imaging parameters. A method for capturing a tomographic image is the same as that employed in step S402 and, therefore, the description thereof is not repeated. At that time, image data of the tomographic image corresponding to the irradiation angle $\theta^i$ used for image capturing is defined as $I_i$. The tomographic image acquiring unit 302 acquires the image data $I_i$ of the captured image from the image capturing unit 101 and stores the image data $I_i$ in the storage unit 306.

<Step S1005>

In step S1005, the shape analyzing unit 303 acquires the image data $I_i$ stored in the storage unit 306 and extracts the surface shape of the optic papilla from the image data $I_i$. A method for extracting the surface shape is the same as that employed in step S403 and, therefore, the description thereof is not repeated. At that time, the surface shape data is defined as $S_i$. Subsequently, the shape analyzing unit 303 sends the image data $I_i$ and the extracted shape data $S_i$ to a luminance information analyzing unit 1305.

<Step S1006>

In step S1006, a selection unit 702 analyzes the luminance information using the image data $I_i$ and the extracted shape data $S_i$ acquired from the shape analyzing unit 303. Thus, the shape analyzing unit 303 computes the luminance evaluation value $V_i$. A method for computing the luminance evaluation value is the same as that employed in step S404 and, therefore, the description thereof is not repeated.

Subsequently, the selection unit 702 stores the luminance evaluation value $V_i$ in the storage unit 306.

<Step S1007>

In step S1007, the selection unit 702 acquires the luminance evaluation value $V_i$ corresponding to the image data $I_i$ stored in the storage unit 306. If the highest value $V_{MAX}$ of the evaluation value is not stored in the storage unit 306, the selection unit 702 performs setting so that $V_{MAX}=V_i$ and stores $V_{MAX}$ in the storage unit 306. However, if the highest value $V_{MAX}$ has already been stored in the storage unit 306, the selection unit 702 compares $V_{MAX}$ with $V_i$. If $V_{MAX}<V_i$, the selection unit 702 updates $V_{MAX}$ so that $V_{MAX}=V_i$ and stores $V_{MAX}$ in the storage unit 306. In addition, the selection unit 702 updates the process number $n_{MAX}$ corresponding to the current $V_{MAX}$ so that $n_{MAX}=i$ and updates the image data $I_{MAX}$ so that $I_{MAX}=I_i$. Thereafter, the selection unit 702 stores $n_{MAX}$ and $I_{MAX}$ in the storage unit 306.

<Step S1008>

In step S1008, the image-capturing instruction unit 901 increments the process number i by one.

<Step S1009>

In step S1009, the image-capturing instruction unit 901 compares the process number i with the number of changes N. If i>N, the image-capturing instruction unit 901 acquires the image data $I_{MAX}$ from the storage unit 306 and sends the image data $I_{MAX}$ to the display unit 103. Thereafter, the processing proceeds to step S1010. However, if i≤N, the processing proceeds to step S1003.

<Step S1010>

In step S1010, the display unit 103 displays the image data $I_{MAX}$ selected by the selection unit 702 on a monitor (not shown).

According to the above-described configuration, a plurality of tomographic images are captured using different irradiation angles in advance, and one of the tomographic images in which the image signal of the surface tissue of the optic papilla including the depressed part is maximized is selected and displayed. Accordingly, the number of image capturing operations can be reduced and, therefore, too much time is not spent on capturing of images. Thus, a tomographic image representing the roughly imaged tissue of the depressed part can be obtained through simplified image analysis.

Third Embodiment

According to the present embodiment, the optic papilla is separated into a plurality of partial areas. An irradiation angle at which the intensity of the signal light beam emitted to the local area is maximized is set for each of the partial areas. Thereafter, a tomographic image is captured using each of the irradiation angles. Subsequently, the captured tomographic images are combined, and the combined image is displayed.

Figure 11:
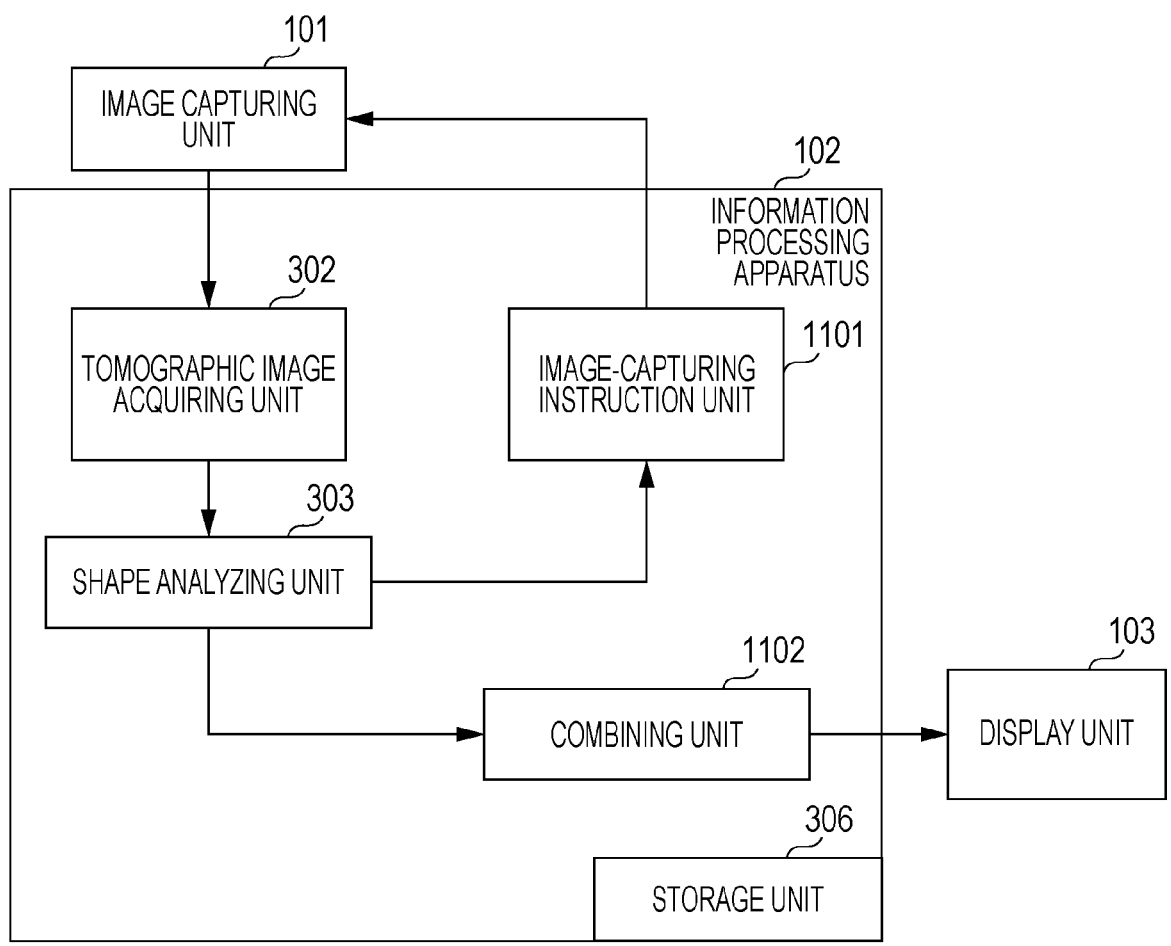
FIG. 11 is a functional block diagram of an OCT imaging apparatus according to a third embodiment.

The function of an information processing apparatus 102 according to the third embodiment is described next with reference to FIG. 11. An image-capturing instruction unit 1101 determines the irradiation angle for each of the local areas as follows. That is, the irradiation angle for each of the local area is set to an angle of the signal light beam that is the closest to a right angle relative to the inner wall of the depressed part in the partial area, that is, the maximum tilt that is physically changeable and that is the closest to a direction perpendicular to the retina surface. This is because as a tilt from the direction perpendicular to the retina surface increases, the irradiation angle relative to the inner wall of the depressed part becomes closer to a right angle. However, in practice, the irradiation angle is limited by the size of the pupil. Accordingly, for each of the partial areas of the optic papilla, a tomographic image that represents the tissue best is acquired. By combining the plurality of acquired tomographic images, a tomographic image that represents all of the tissues of the depressed part best can be obtained. More specifically, the signal light beam is made incident from an extension part of the pupil.

A combining unit 1102 combines the plurality of acquired tomographic images. For each of the tomographic images $I_1$ to $I_N$ captured by the image capturing unit 101, the reference irradiation direction $D_0$ is associated with the image data I of the tomographic image using a method that is the same as that in step S901 in the first embodiment. Since the image data items $I_1$ to $I_N$ represent images captured by tilting the signal light beam at angles of $\theta^1$ to $\theta^N$ with respect to the reference irradiation direction $D_0$, positioning is performed by rotating the images by angles of $\theta^1$ to $\theta^N$ so that the reference irradiation directions $D_0$ of the image data items are aligned. Thereafter, the pixel values of corresponding pixels of the image data items $I_1$ to $I_N$ after the positioning is performed are combined. Thus, combined image data $I_C$ is generated. According to a method for combining the pixel values of the present embodiment, an average of the pixel values is defined as a new pixel value after the combining operation is performed. In addition, a combined image is generated so that the z-axis is aligned with the direction $D_0$. At that time, the pixels in the image data items $I_1$ to $I_N$ that are not included in the range of the tomographic image after the combining operation is performed are not combined. In this way, since the plurality of tomographic images to be combined are captured at different angles, a combined image in which the area having a low intensity of the signal of one image is replaced with the area having a high intensity of the signal of a different image can be obtained. However, a method for combining the tomographic images is not limited thereto. For example, the reliability may be assigned to each of the pixels in accordance with the magnitude of the luminance value of the pixel. The weighted average value obtained using the reliability as a coefficient may be used as a new pixel value after the combining operation is performed. In such a case, the area having a low signal intensity can be more accurately compensated for.

Figure 12:
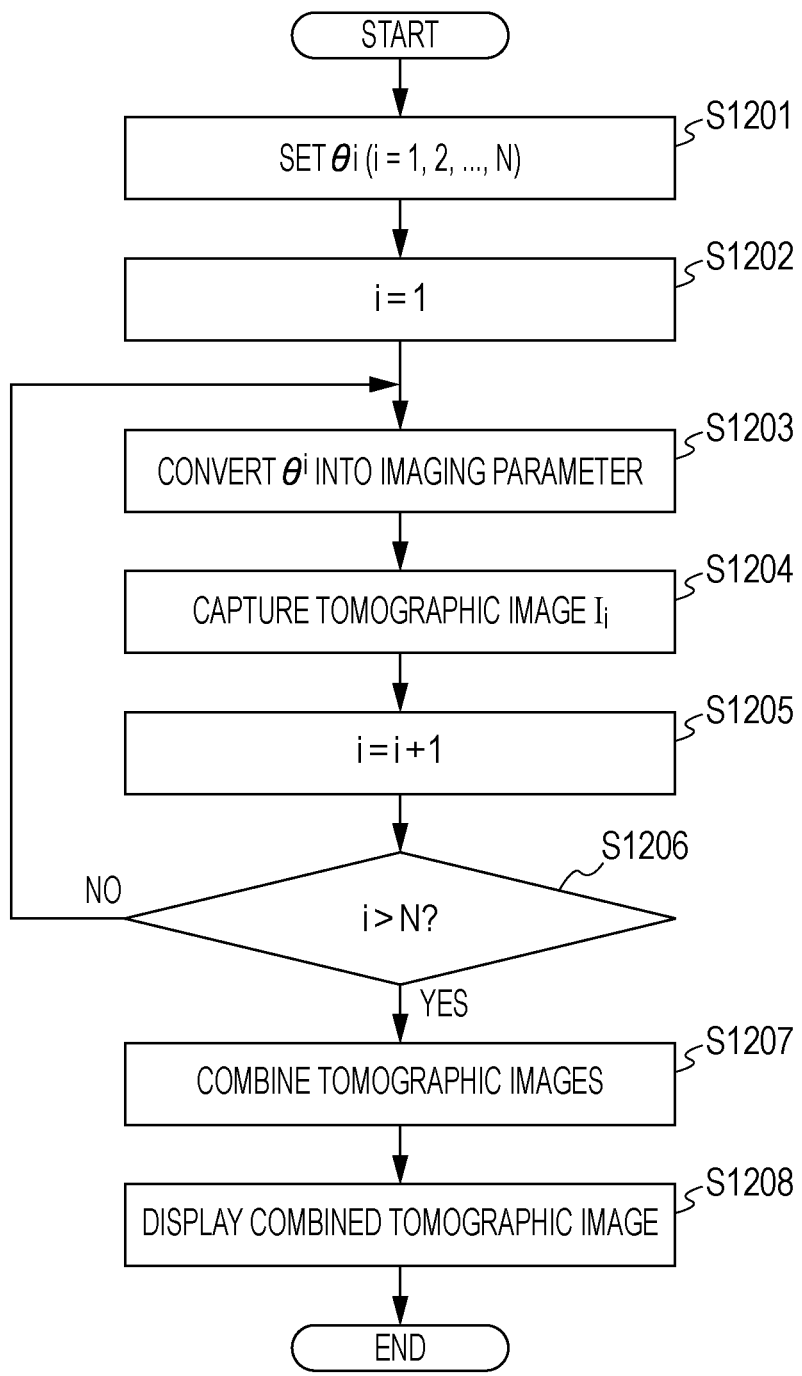
FIG. 12 is a flowchart illustrating the procedure of processing performed by an information processing apparatus 102 according to the third embodiment.

The procedure of processing performed by the information processing apparatus 102 according to the present embodiment is described next with reference to a flowchart shown in FIG. 12. Note that since steps S1202, S1203, S1204, S1205, and S1206 are similar to steps S1002, S1003, S1004, S1008, and S1009 of the second embodiment, respectively, the descriptions thereof are not repeated.

<Step S1201>

In step S1201, the image-capturing instruction unit 1101 generates the instruction information 1. Thereafter, the image-capturing instruction unit 1101 defines the number of changes in irradiation angle as N and sets changed irradiation angles $\theta^1$ to $\theta^N$. Thereafter, the image-capturing instruction unit 1101 stores these values. According to the present embodiment, for irradiation angles $\theta^1$ to $\theta^N$, $\theta_1$ is divided into equal angles in the possible range. However, in order to make the signal light beam incident from an extension part of the pupil, the value of $\theta_2$ is fixed so that $\theta_2 = \theta_{LIM}$. The area 503 and the area 504 in which the intensity of the image signal is significantly low are represented.

Figure 13A:
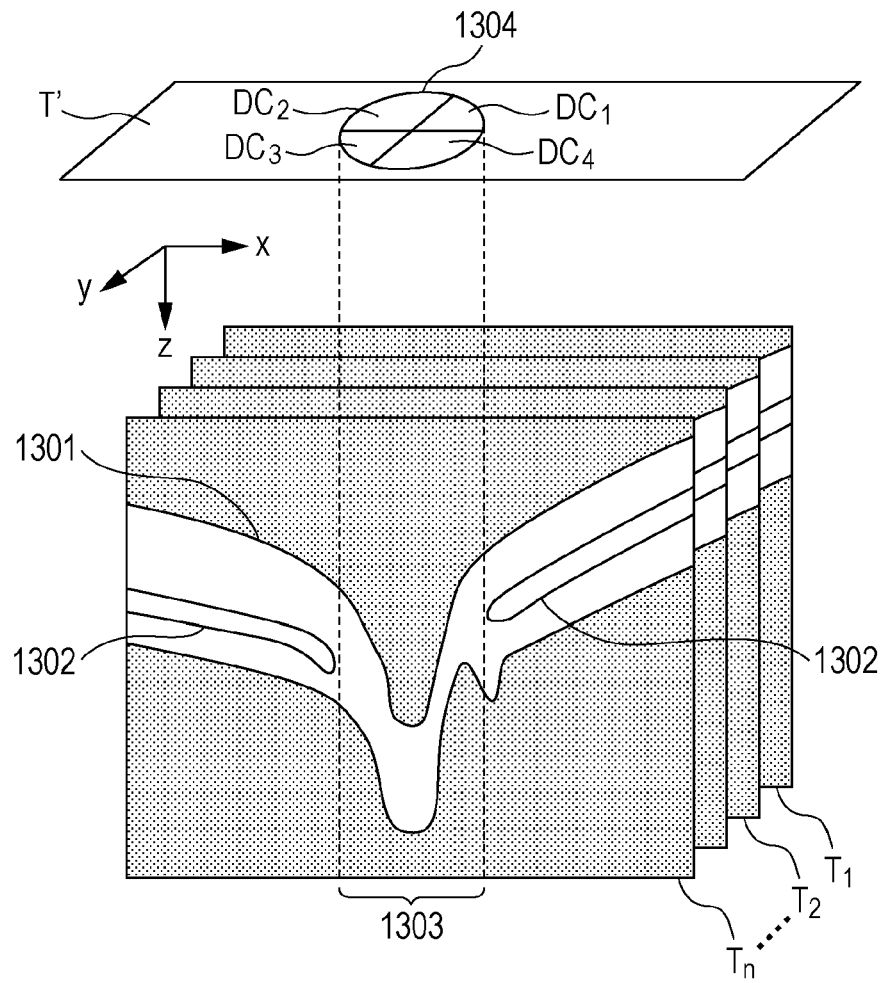
FIGS. 13A and 13B illustrate a direction in which a signal light beam is emitted for each of partial areas of a target tissue.
Figure 13B:
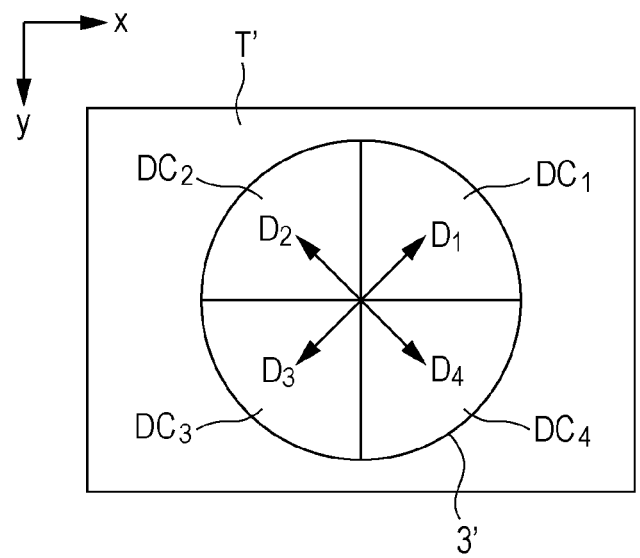
Figure 14:
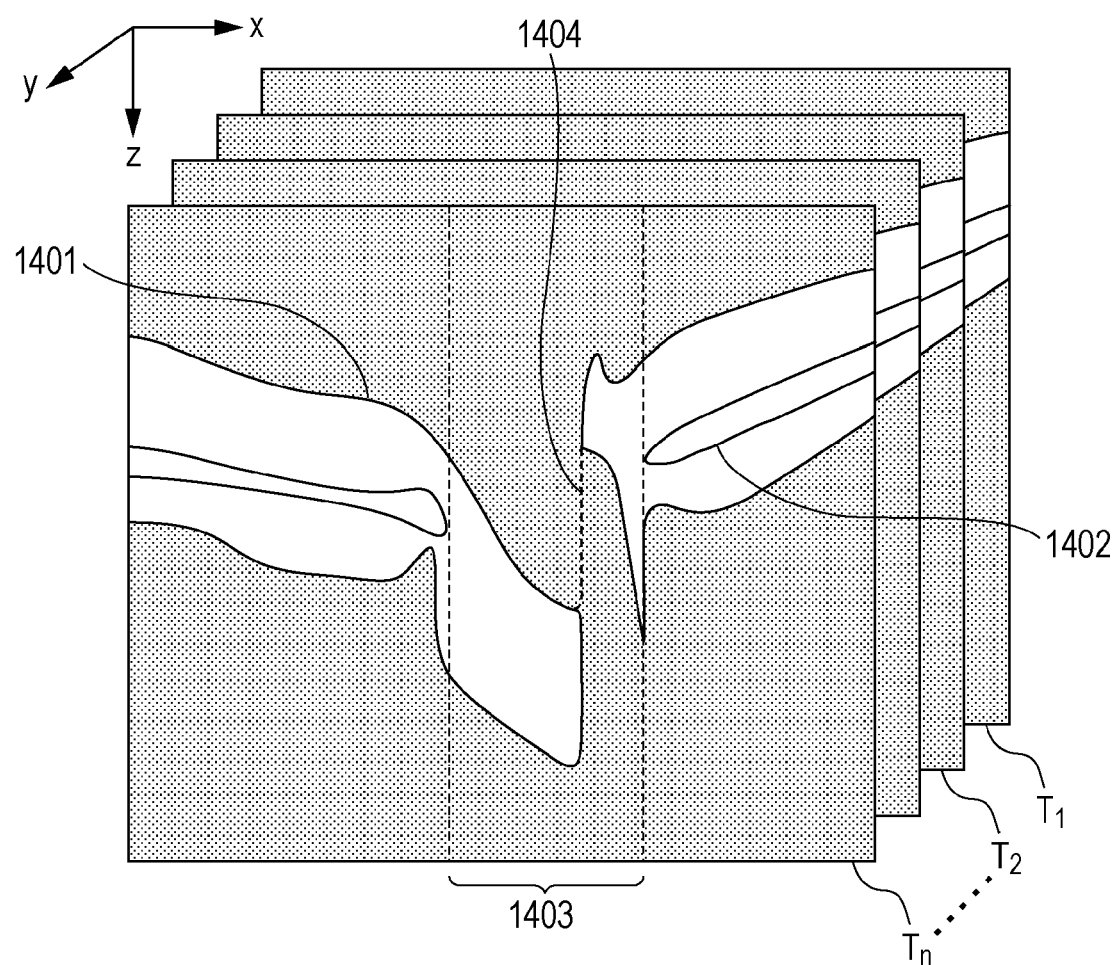
FIG. 14 is a schematic illustration of tomographic images indicating a case in which the optic papilla is diagonally depressed.

In FIG. 13A, tomographic images $T_1$ to $T_n$, an inner limiting membrane 1301, a pigment layer of the retina 1302, and an optic papilla area 1303 are shown. In addition, a plane T' parallel to the x-y plane, a projection area 1304 corresponding to the optic papilla area 1303 when the tomographic images $T_1$ to $T_n$ are projected to the plane T', and partial areas $DC_1$ to $DC_4$ obtained by dividing the projection area 1304 into equal partial areas are shown. In this example, the division number n=4. According to the present embodiment, for each of the surfaces areas of the depressed part that belong to the areas $DC_1$ to $DC_4$, an irradiation angle at which the intensity of the signal light beam emitted to the surface area is set. FIG. 13B illustrates the plane T' shown in FIG. 13A viewed from the z-axis direction. In FIG. 13B, $D_1$ to $D_4$ denote irradiation angles at which the intensities of the signal light beams emitted to the areas $DC_1$ to $DC_4$ in the plane T' are maximized, respectively. Since the irradiation angle of the signal light beam projected to the x-y plane is expressed by the angle component $\theta_1$, angles of $\theta_1$ corresponding to $D_1$ to $D_4$ are expressed as $\theta_1^1$ to $\theta_1^4$ (an angle obtained by dividing the range from 0° to 360° into four equal angles), respectively. In addition, as the signal light beam emitted to the surface of the depressed part becomes closer to a direction perpendicular to the surface, the intensity of the signal light beam emitted to the wall of the depressed part increases. Accordingly, since the tilt of the irradiation angle of the signal light beam is determined by the angle component $\theta_2$, $\theta_2$ is set to a constant value of the maximum angle $\theta_{LIM}$, which is a maximum angle of physically possible angles relative to the surface of the retina. As described above, by acquiring a tomographic image corresponding to each of the signal light beams emitted from a plurality of points in the extension part of retina, a tomographic image in which the intensity of the signal light beam of each of the areas of the depressed part is increased can be obtained.

Subsequently, the image-capturing instruction unit 1101 sends the acquired instruction information 1 to the image capturing unit 101.

<Step S1207>

In step S1207, the combining unit 1102 acquires the image data items $I_1$ to $I_N$ of the tomographic images from the storage unit 306 and generates a combined image. A method for combining the images is the same as that described above. Thereafter, the combining unit 1102 sends image data $I_C$ of the generated combined image to the display unit 103.

<Step S1208>

In step S1208, the display unit 103 displays the image data $I_C$ acquired from a tomographic image combining unit 1102.

According to the above-described configuration, the irradiation angle at which the intensity of the signal light beam is maximized is determined for each of partial areas of the optic papilla. Thereafter, tomographic images are captured using these angles and are combined. In this way, a tomographic image in which the tissue of the depressed part is uniformly excellently presented can be provided. In addition, as in the first and second embodiments, the need for an image analyzing process required after a tomographic image is captured can be eliminated.

Other Embodiment

According to the first embodiment, if the luminance evaluation value V of a tomographic image captured first is smaller than the threshold value, the irradiation angle $\theta_{MAX}$ is obtained. Subsequently, a tomographic image is captured using this angle only once, and the tomographic image is presented without any modification. However, the number of re-image capturing operations is not limited to one. For example, in FIG. 4, an arrow from step S402 to step S407 may be added, and the processes in steps S402 to S407 may be repeated until the luminance evaluation value V obtained in step S405 exceeds the threshold value. This is because the irradiation angle $\theta_{MAX}$ is optimized by the re-image capturing angle determination unit 305 on the basis of the image data of the tomographic image captured at that time. Therefore, the surface shape of an area of the depressed part in which the intensity of the image signal is low may not be correctly extracted. In this case, since the irradiation angle $\theta_{MAX}$ has not been obtained using the correct surface shape of the depressed part, the image of the depressed part may not be sufficiently captured. In contrast, the image is captured again using the obtained irradiation angle $\theta_{MAX}$, and a tomographic image including the more correctly captured image of the depressed part is obtained. Thereafter, the image is evaluated and analyzed. In this way, finally displaying of a tomographic image captured using an irradiation angle at which the image of the depressed part is not precisely captured can be prevented.

While the first to third embodiments have been described with reference to the example in which the present invention is applied in order to correctly extract the shape of the depressed part of the optic papilla, applications of the present invention are not limited thereto. For example, some of the features of the present invention described herein, that is, the method for analyzing a shape and a method for computing the intensity of a signal, are applicable to extract the shape of a boundary between layers. For example, the methods are applicable to extract a layer present in an area under the blood vessels that was not previously possible to be imaged or a boundary surface.

In addition, an OCT imaging apparatus that captures an image in response to an instruction received from the information apparatus according to the present invention is not limited to that described above. While the present embodiment has been described with reference to a single beam OCT, a multi-beam OCT can be employed.

Furthermore, the present invention can also be achieved by supplying a program that realizes the functions of the above-described embodiments to a system or an apparatus via a network or a variety of recording media and by causing a computer (or a CPU) of the system or apparatus to read out and execute the program. In such a case, the program supplied to the apparatus or the system or the recording medium storing the program constitutes the present invention.

In such a configuration, a signal light beam is emitted at an angle at which the object to be imaged has a predetermined signal intensity in accordance with at least part of the shape of the object to be imaged and a tomographic image is captured. Accordingly, a tomographic image by which the layer structure of the object is correctly identified can be acquired.

BRIEF DESCRIPTION OF DRAWINGS

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of International Application No. PCT/JP2009/068619, filed Oct. 29, 2009, hereby incorporated by reference herein in its entirety.

Reference Signs List
101 image capturing unit
102 information processing apparatus
118 CPU
119 RAM
120 ROM
301 image-capturing instruction unit
302 tomographic image acquiring unit
303 shape analyzing unit
304 re-image capturing determination unit
305 re-image capturing angle determination unit

The invention claimed is:

1. An information processing apparatus comprising:
a determination unit configured to determine an incident angle of a signal light beam made incident on an object to be imaged in accordance with a structure of the object to be imaged; and an instruction unit configured to send instructions to change an incident angle of a signal light beam made incident on an object to be imaged based on the determined incident angle, and to capture a tomographic image of the object to be imaged;
wherein the determination unit determines the irradiation angle of the signal light beam so that an area in which the intensity of the signal light beam emitted to the object to be imaged is lower than a reference value is decreased in accordance with the shape of the object to be imaged.

2. The information processing apparatus according to claim 1, further comprising:
an acquiring unit configured to acquire the tomographic image of the object to be imaged captured on the basis of a returning light beam of a signal light beam emitted to the object to be imaged at a predetermined angle;
wherein the determination unit determines the shape of the object to be imaged on the basis of the acquired tomographic image.

3. The information processing apparatus according to claim 2, wherein if the predetermined angle is the same as the determined angle, the instruction is not sent from the instruction unit.

4. The information processing apparatus according to claim 2, further comprising:
a determining unit configured to determine whether the instruction is sent by the instruction unit in accordance with, in the acquired tomographic image, a size of one of an area in which the intensity of the returning light beam is lower than a reference value, an area in which the shape of the object to be imaged was unable to be identified, an area in which the shape of the object to be imaged is estimated through interpolation, and an area in which a reliability of the shape is low.

5. The information processing apparatus according to claim 1, wherein the object to be imaged is a boundary surface between layers of a retina, and wherein the determination unit evaluates the intensity of the signal light beam in accordance with an incident angle of the signal light beam onto each area of the boundary surface.

6. The information processing apparatus according to claim 1, wherein the object to be imaged is a depressed part of a retina, and wherein the determination unit determines the irradiation angle in accordance with a tilt of the depressed part relative to the surface of the retina.

7. The information processing apparatus according to claim 1, wherein the instruction unit sends one of information indicating that image capturing is to be performed, an imaging condition used for an image capturing unit, and an instruction to capture an image.

8. The information processing apparatus according to claim 1, wherein the tomographic image is captured by an optical coherence tomographic imaging apparatus that separates a light beam into a signal light beam and a reference light beam, leads the signal light beam to an object to be imaged, leads the reference light beam to a reference mirror, and captures a tomographic image using a returning light beam of the signal light beam reflected or scattered by the object to be imaged and the reference light beam reflected by the reference mirror.

9. An information processing apparatus comprising:
a setting unit configured to set a plurality of incident angles of a signal light beam made incident on an object to be imaged;
a determination unit configured to determine the irradiation angle of the signal light beam so that an area in which the intensity of the signal light beam emitted to the object to be imaged is lower than a reference value is decreased in accordance with the shape of the object to be imaged;
an acquiring unit configured to acquire a plurality of tomographic images of an object to be imaged using returning light beams of the signal light beam for scanning the object to be imaged while changing an incident angle of the signal light based on the incident angles which has been set by the setting unit; and
a selecting unit configured to select at least one tomographic image from among the plurality of acquired tomographic images in accordance with a size of an area of the acquired tomographic images in which an intensity of the returning light beam is lower than a predetermined reference value.

10. The information processing apparatus according to claim 9, wherein the selecting unit evaluates the intensity of the returning light beam on the basis of one of a luminance value and an S/N ratio of the tomographic image.

11. The information processing apparatus according to claim 9, wherein the object to be imaged is a retina, and wherein the signal light beam is irradiated on the retina at a plurality of different angles by making the signal light beam incident on a plurality of positions in extension part of a pupil.

12. An information processing apparatus comprising:
an acquiring unit configured to acquire a plurality of tomographic images each generated using a returning light beam of a signal light beam emitted to an object to be imaged at a preset angle, the plurality of tomographic images being acquired by changing the angle;
a determination unit configured to determine the irradiation angle of the signal light beam so that an area in which the intensity of the signal light beam emitted to the object to be imaged is lower than a reference value is decreased in accordance with the shape of the object to be imaged; and a combining unit configured to combine the acquired tomographic images of the object to be imaged.

13. An information processing apparatus comprising:
an identifying unit configured to identify the shape of a depressed part of a retina of an eye to be examined;
a determination unit configured to determine an irradiation angle of a signal light beam emitted to the depressed part so that a returning light beam of the signal light beam emitted to the depressed part on the basis of the identified shape of the depressed part has a predetermined intensity; and
an acquiring unit configured to acquire a tomographic image representing the depressed part by generating an interference light beam on the basis of the returning light beam of the signal light beam emitted at the determined irradiation angle.

14. An information processing apparatus comprising:
an acquiring unit configured to acquire a plurality of tomographic images using returning light beams of a signal light beam emitted to a retina at a plurality of different angles;
a determination unit configured to determine the irradiation angle of the signal light beam so that an area in which the intensity of the signal light beam emitted to the object to be imaged is lower than a reference value is decreased in accordance with the shape of the object to be imaged; and
a combining unit configured to combine the acquired tomographic images;
wherein the signal light beam is irradiated to the retina at a plurality of different angles by making the signal light beam incident on a plurality of positions in an extension part of a pupil.

15. An information processing apparatus for separating a light beam emitted from a light source into a signal light beam and a reference light beam, leading the signal light beam to an object to be imaged, leading the reference light beam to a reference mirror, and combining tomographic images generated using an interference light beam of a returning light beam of the signal light beam reflected or scattered by the object to be imaged and the reference light beam reflected by the reference mirror, the information processing apparatus comprising:
a determination unit configured to determine the irradiation angle of the signal light beam so that an area in which the intensity of the signal light beam emitted to the object to be imaged is lower than a reference value is decreased in accordance with the shape of the object to be imaged;
an acquiring unit configured to acquire a plurality of tomographic images using returning light beams of the signal light beam emitted to the object to be imaged at a plurality of different angles; and
a combining unit configured to combine the plurality of acquired tomographic images.

16. A method for processing information, comprising the steps of:
determining an irradiation angle of a signal light beam emitted to an object to be imaged in accordance with a shape of the object to be imaged so that a returning light beam of the signal light beam has a predetermined intensity; and
sending instructions to change an incident angle of a signal light beam made incident on an object to be imaged based on the determined incident angle, and to capture a tomographic image of the object to be imaged.

17. A non-transitory computer storage readable medium comprising:
a program for causing a computer to perform processes for determining an irradiation angle of a signal light beam emitted to an object to be imaged in accordance with a shape of the object to be imaged so that a returning light beam of the signal light beam has a predetermined intensity and sending instructions to change an incident angle of a signal light beam made incident on an object to be imaged based on the determined incident angle, and to capture a tomographic image of the object to be imaged.

18. An imaging system comprising:
an image pickup unit configured to acquire a tomographic image by capturing an image of an object to be imaged using a returning light beam of a signal light beam emitted to the object to be imaged at a predetermined angle;
an acquiring unit configured to acquire a tomographic image of the object to be imaged captured on the basis of a returning light beam of a signal light beam emitted to the object to be imaged at a first irradiation angle;
an analyzing unit configured to analyze a shape of the object to be imaged using the acquired tomographic image;
an instruction unit configured to instruct the image pickup unit to change an incident angle of a signal light beam made incident on an object to be imaged based on the determined incident angle, and to capture an image of the object to be imaged by emitting the signal light beam to the object to be imaged at a second irradiation angle different from the first irradiation angle in accordance with a result of the analysis; and
a display unit configured to display the tomographic image captured by the image pickup unit in response to the instruction sent from the instruction unit.

19. An information processing apparatus comprising:
a determination unit configured to determine an incident angle of a signal light beam made incident on an object to be imaged in accordance with a structure of the object to be imaged; and
an instruction unit configured to send instructions to change an incident angle of a signal light beam made incident on an object to be imaged based on the determined incident angle, and to capture a tomographic image of the object to be imaged.

20. An information processing apparatus comprising:
a setting unit configured to set a plurality of incident angles of a signal light beam made incident on an object to be imaged;
an acquiring unit configured to acquire a plurality of tomographic images of an object to be imaged using returning light beams of the signal light beam for scanning the object to be imaged while changing an incident angle of the signal light based on the incident angles which has been set by the setting unit; and
a selecting unit configured to select at least one tomographic image from among the plurality of acquired tomographic images in accordance with a size of an area of the acquired tomographic images in which an intensity of the returning light beam is lower than a predetermined reference value.

21. An information processing apparatus comprising:
an acquiring unit configured to acquire a plurality of tomographic images each generated using a returning light beam of a signal light beam emitted to an object to be imaged at a preset angle, the plurality of tomographic images being acquired by changing the angle;

a combining unit configured to combine the acquired tomographic images of the object to be imaged.

22. An information processing apparatus comprising:
an acquiring unit configured to acquire a plurality of tomographic images using returning light beams of a signal light beam emitted to a retina at a plurality of different angles; and
a combining unit configured to combine the acquired tomographic images;
wherein the signal light beam is irradiated to the retina at a plurality of different angles by making the signal light beam incident on a plurality of positions in an extension part of a pupil.

23. An information processing apparatus for separating a light beam emitted from a light source into a signal light beam and a reference light beam, leading the signal light beam to an object to be imaged, leading the reference light beam to a reference mirror, and combining tomographic images generated using an interference light beam of a returning light beam of the signal light beam reflected or scattered by the object to be imaged and the reference light beam reflected by the reference mirror, the information processing apparatus comprising:
an acquiring unit configured to acquire a plurality of tomographic images using returning light beams of the signal light beam emitted to the object to be imaged at a plurality of different angles; and
a combining unit configured to combine the plurality of acquired tomographic images.

24. An image capturing apparatus for performing optical coherence tomography, the image capturing apparatus comprising:
a control unit configured to perform a control operation to change an incident angle of a measurement light beam incident on an object to be imaged based on an image of a person to be examined; and
an image generation unit configured to acquire a tomographic image of a retina based on a returning light beam of the measurement light beam incident on the object to be imaged according to the control operation.

25. The image capturing apparatus according to claim 24, wherein the control unit is configured to change the incident angle of the measurement light beam incident on the object to be imaged based on image quality of the tomographic image generated by the image capturing apparatus.

26. The image capturing apparatus according to claim 25, wherein the control unit is configured to change the incident angle of the measurement light beam incident on the object to be imaged based on an S/N ratio of the tomographic image generated by the image capturing apparatus.

27. The image capturing apparatus according to claim 24, wherein the control unit is configured to change the incident angle of the measurement light beam incident on the object to be imaged based on luminance information of the tomographic image generated by the image capturing apparatus.

28. The image capturing apparatus according to claim 27, wherein the control unit is configured to change the incident angle of the measurement light beam incident on the object to be imaged based on a luminance value of the object to be imaged in the tomographic image generated by the image capturing apparatus.

29. The image capturing apparatus according to claim 28, wherein the tomographic image generated by the image capturing apparatus is a two-dimensional image to be acquired by horizontally arranging A-scan data along a depth direction, and
wherein the incident angle of the measurement light beam incident on the object to be imaged is changed based on a tilt of a line to be obtained by connecting, in the two-dimensional image, points at which a luminance value is equal to or larger than a predetermined value in the A-scan data.

30. The image capturing apparatus according to claim 24, wherein
wherein the control unit is configured to change the incident angle of the measurement light beam incident on the object to be imaged based on a tilt of a retina that is the object to be imaged in the tomographic image.

31. The image capturing apparatus according to claim 30, wherein the control unit is configured to change the incident angle of the measurement light beam incident on a retina based on a tilt of a specific structure of the retina that is the object to be imaged in the tomographic image.

32. The image capturing apparatus according to claim 31, wherein the control unit is configured to change the incident angle of the measurement light beam incident on the object to be imaged based on a tilt of an inner limiting membrane in the tomographic image.

33. The image capturing apparatus according to claim 24, wherein the image generation unit is configured to generate a first tomographic image,
wherein the control unit is configured to change the incident angle of the measurement light beam to a second incident angle different from a first incident angle based on the first tomographic image, and
wherein the image generation unit is configured to acquire a tomographic image of the retina based on a returning light beam of the measurement light beam incident on the object to be imaged after the incident angle is changed.

34. The image capturing apparatus according to claim 24, wherein the object to be imaged is fundus of a person to be examined, and
wherein the control unit is configured to change the incident angle of the measurement light beam incident on the fundus by changing an incident position at which the measurement light beam is incident on a pupil of the person to be examined.

35. A control method of optical coherence tomography, the method comprising:
changing an incident angle of a measurement light beam incident on an object to be imaged based on an image of a person to be examined; and
generating a tomographic image of a retina based on a returning light beam of the measurement light beam incident on the object to be imaged after the incident angle is changed.

36. A program for causing a computer to execute the control method according to claim 35.

37. An information processing apparatus for controlling optical coherence tomography, the information processing apparatus comprising:
an instruction unit configured to output an instruction to change an incident angle of a measurement light beam incident on an object to be imaged based on an image of a person to be examined; and
an acquisition unit configured to acquire a tomographic image of a retina obtained based on a returning light beam of the measurement light beam incident on the object to be imaged after the incident angle is changed.

38. An image capturing apparatus for performing optical coherence tomography, the image capturing apparatus comprising:
- a control unit configured to change a position of a fixation lamp based on an image of fundus; and
- an image generation unit configured to acquire a tomographic image of a retina based on a returning light beam of a measurement light beam incident on an object to be imaged after an incident angle is changed.

* * * * *